United States Patent [19]

Tsuji et al.

[11] Patent Number: 5,854,042
[45] Date of Patent: Dec. 29, 1998

[54] SUGAR-CHAIN SYNTHETASE AND PROCESS FOR PRODUCING THE SAME

[75] Inventors: Shuichi Tsuji; Nobuyuki Kurosawa; Toshiro Hamamoto; Young-Choon Lee; Takashi Nakaoka; Naoya Kojima, all of Saitama, Japan

[73] Assignee: The Institute of Physical and Chemical Research, Saitama, Japan

[21] Appl. No.: 666,367

[22] PCT Filed: Dec. 22, 1994

[86] PCT No.: PCT/JP94/02182

§ 371 Date: Aug. 19, 1996

§ 102(e) Date: Aug. 19, 1996

[87] PCT Pub. No.: WO95/18217

PCT Pub. Date: Jul. 6, 1995

[30] Foreign Application Priority Data

Dec. 24, 1993 [JP] Japan .................................... 5-348260
Mar. 28, 1994 [JP] Japan .................................... 6-057369
Apr. 28, 1994 [JP] Japan .................................... 6-091507

[51] Int. Cl.$^6$ .................................................. C12N 9/10
[52] U.S. Cl. .......................................... 435/193; 435/69.7
[58] Field of Search .................................... 435/193, 69.7

[56] References Cited

PUBLICATIONS

J. Weinstein et al. "Primary Structure of β–Galactoside α2,6–Sialytransferase", The Journal of Biological Chemistry, vol. 262, No. 36, pp. 17735–17743, Dec. 25, 1987.

D. Wen et al. "Primary Structure of Galβ1,3(4)GlcNAc α2,3–Sialyltransferase Determined by Mass Spectrometry Sequence Analysis and Molecular Cloning", The Journal of Biological Chemistry, vol. 267, No. 29, pp. 21011–21019, Oct. 15, 1992.

W. Gillespie et al. "Cloning and Expression of the Galβ1, 3GalNAc α2,3–Sialytransferase", The Journal of Biological Chemistry, vol. 267, No. 29, pp. 21004–21010, Oct. 15, 1992.

S. Hakomori, "Glycosphingolipids in Cellular Interaction, Differentiation, and Oncogenesis[1]", Ann. Rev. Biochem., vol. 50, pp. 733–764, 1981.

Blumenfeld, O. O., et. al. (1992) Blood 80(9), 2388–2395.

Gross, H. J., et. al. (1989) Biochemistry 28, 7386–7392.

Gross, H. J., et. al. (1988) Eur. J. Biochem. 177, 583–589.

Higa, H. H., et. al. (1985) J. Biol. Chem. 260(15),8839–8849.

Kurosawa, N, et. al. (1994) J. Biol. Chem. 269(2), 1402–1409.

Kurosawa, N, et. al. (1994) J. Biol. Chem. 269(29), 19048–19053.

J. Sadler et al., "Purification to Homogeneity of a β–Galactoside α2 → 3 Sialytransferase and Partial Purification of an α–N–Acetylgalactosaminide α2→6 Sialytransferase from Porcine Submaxillary Glands", The Journal of Biological Chemistry, vol. 254, No. 11, Jun. 10, 1979, pp. 4434–4443.

J. Sadler et al., "Purification to Homogeneity and Enzymatic Characterization of an α–N–Acetylgalactosaminide α2 → 6 Sialytransferase from Porcine Submaxillary Glands", The Journal of Biological Chemistry, vol. 254, No. 13, Jul. 10, 1979, pp. 5934–5941.

Primary Examiner—Charles L. Patterson, Jr.
Attorney, Agent, or Firm—Wenderoth, Lind & Ponack, LLP

[57] ABSTRACT

Novel GalNAc α 2,6-sialyltransferases P-B1 and P-B3; GalNAc α 2,6-sialyltransferase genes encoding the above GalNAc α 2,6-sialyltransferases P-B1 and P-B3; and an extracellularly releasable protein catalyzing GalNAc α 2,6-sialic acid transfer which comprises a polypeptide portion as being an active domain of the GalNAc α 2,6-sialyltransferase P-B1 or P-B3 together with a signal peptide are provided. Also provided is a process for preparing a sialyltransferases which enables efficient recovery of a sialyltransferase expressed in a large quantity in microorganisms.

18 Claims, 4 Drawing Sheets

FIG. 4

```
P-B3  - MG--------SPRWKRFCFLLLAAFTSSLLLYGHYYATVDVRSGPRVTSLLQPELLFLVRPDTPHPDNSHHKELRGTVKSREFFSQPSSELEKPKPSG  - 91
         ||                                                
P-B1  - MGFLIRRLPKDSRIFRWLLILTVFSFIITSFSALFGMEKSIFRQLKIYQSIAHMLQVDTQDQQGSNYSANGRISKVGLERDIAWLELNTAVSTPSGEGKE -100

P-B3  - KQPTPCPRSVAATAKADPTFGELFQFDIPVLM--------------------------------------------------------------- -123
         | |                                                
P-B1  - EQKKTVKPVAKVEEAKEKVTVKPFPEVMGITNTTASTASVVERTKEKTTARPVPGVGEADGKRTTIALPSMKEDKEKATVKPSFGMKVAHANSTSKDKPK -200

P-B3  - ------------------------------------------------------------------------------------------------ -123

P-B1  - AEEPPASVKAIRPVTQAATVTEKKLRAADFKTEPQWDFDDEYILDSSSPVSTCSESVRAKAAKSDWLRDLFLPNITLFIDKSYFNVSEWDRLEHFAPPY -300

P-B3  - WDQHFNPETWDRLKARRVPYGWQGLSQAAVGSTLRLFDRHLFPGGC⎡RCAVVGNGGILNGSRQGRAIDAHDLVFRLNGAITKGFEEDVGSKV⎤SFYGFTVN -223
         ||||  ||| |   ||    | | |   | |   |||| |   ⎢|||||||||||  ||  ||    | | |   |||| |   ⎢|||||||
P-B1  - GFMELNYSLVEEVMSRLPPNPHQQLLANSSSNVSTLNTSSNTRLC⎣SCAVVGNGGILNNSGMGQEIDSHDYVFRVSGAVIKGYEKDVGTKI⎦SFYGFTAY -400

P-B3  - TMKNSLIAYEAYGFTRTPQGKDLKYIFIPSDARDYIMLRSAIQGSPVPEG-LDKGDEPQKYFGLEASAEKFKLL-HPDFLHYLTTRFLRSELLDMQYGHL -321
         | |     |  | |  | | |||  |   |  | | | |                | |  |   | |  |     ||||| |  |         
P-B1  - SLVSSLQNLGHKGFKKIPQGKHIRYIHFLEAVRDYEWLKALLLDKDIRKGFLNYYGRRPRERFDEDFTMNKYLVAHPDFLRYLKNRFLKSKNLQKPYWRL -500

P-B3  - YM⎡PSTGALMLLTALHTCDQVSAYGF⎤ITANYEQFSDHYYEPEKKPLVFYANHDMLLEAELWRSLHRAGIMELYQR -404
         ||⎢|| ||| ||| ||| |||||||⎥|  |    |||  |  |||| | | ||              | 
P-B1  - YR⎣PTTGALLLTALHLCDRVSAYGY⎦ITEGHQKYSDHYYDKEWKRLVFYVNHDFNLEKQVWKRLHDENIMKLYQRS -566
```

SUGAR-CHAIN SYNTHETASE AND PROCESS FOR PRODUCING THE SAME

BACKGROUND OF THE INVENTION

1. Field of the Invention

The present invention relates to a sugar-chain synthetase and a DNA encoding the enzyme. More specifically, the present invention relates to an N-acetylgalactosamine α 2,6-sialyltransferase (GalNAc α 2,6-sialyltransferase) and a DNA encoding the enzyme. The enzyme is useful as medicaments having inhibitory activities against tumor metastases and viral infection, and as agents for introducing a sialic acid moieties into drugs to increase their biological activity.

The present invention further relates to a process for producing the sugar-chain synthetase. More specifically, the present invention relates to a process for expressing sialyltransferases in microorganisms to obtain the sialyltransferases in large quantities.

2. Decription of Related Art

Sialic acids play an important role in a variety of biological processes, like cell-cell communication, cell-substrate interaction, adhesion. It has been known that various kinds of distinguishable cell surface sialic acids exist which change in a regulated manner during development, differentiation, and oncogenic transformation.

Sialic acids occur at the terminal positions of the carbohydrate groups of glycoproteins and glycolipids, and they are enzymatically introduced from CMP-Sia to these positions in a post translational process. For example, three linkage patterns, Sia α 2,6Gal, Sia α 2,3Gal and Sia α 2,6GalNAc are commonly found in glycoproteins (Hakomori, S., Ann. Rev. Biochem., 50, pp.733–764, 1981), and two, Sia α 2,3Gal and Sia α 2,8Sia, occur frequently in gangliosides (Fishman, P., and Brady, R. O., Science, 194, pp.906–915, 1976).

The enzymes responsible for such enzymatic introduction of sialic acid (sialic acid transfer) as mentioned above are glycosyltransferases called sialyltransferases. It has been known that at least 12 different sialyltransferases are required to synthesize all known sialyloligosaccharide structures (Broquet, P. et al., Int. J. Biochem., 23, 385–389, 1991; and Weinstein, J. et al., J. Biol. Chem., 262, 17735–17743, 1987). Among these enzymes, five sialyltransferases have been purified so far, and it has been known that they exhibit strict specificity for acceptor substrate (Sadler, J. et al., J. Bio. Chem., 254, pp.4434–4443, 1979; Weinstein, J. et al., J. Biol. Chem., 257, pp.13835–13844, 1982; Rearick, J. et al., J. Biol. Chem., 254, pp.4444–4451, 1979; and Joqiasse, D. H. et al., J. Biol. Chem., 260, 4941–4951, 1985).

As for cDNAs encoding the aforementioned sialyltransferases, cDNAs encoding Gal β 1,4GlcNAc α 2,6-sialyltransferase (Gal β 4GlcNAc-α 6ST) have been cloned from various organs including liver (Weinstein, J. et al., J. Biol. Chem., 262, pp.17735–17743, 1987; Grundmann U. et al., Nucleic Acids Res. 18, 667, 1990; Bast, B. et al., J. Cell. Biol., 116, pp.423–435, 1992; and Hamamoto, T. et al., Bioorg. and Medic. Chem., 1, pp.141–145, 1993). Furthermore, cDNAs encoding Gal β 1,3GalNAc α 2,3-sialyltransferase (Gal β 3GalNAc-α 3ST) (Gillespie, W. et al., J. Biol. Chem., 267, pp.21004–21010, 1992: Japanese Patent Unexamined Publication No. 5-504678/1993; and Lee, Y. et al., Eur. J. Biochem, 216, 377–385, 1993); Gal β 1,3(4) GlcNAc α 2,3-sialyltransferase (Gal β 3(4)GlcNAc-α 3ST) (Wen, D. X et al., J. Biol. Chem., 267, 21011–21019, 1992; and Kitagawa, H. et al., Biochem. Biophys. Res. Commun. 194, 375); and Gal β 1,3GalNAc/Gal β 1,4GlcNAc α 2,3-sialyltransferase (Sasaki, K. et al., J. Biol. Chem., 268, 22782–22787, 1993) have also been cloned.

With respect to GalNAc α 2,6-sialyltransferase, the isolation of this enzyme has been reported (Hakomori, S., Ann. Rev. Biochem., 50, 733–764, 1981). However, the enzyme has not been purified so as to be characterized as a single identifiable substance, and accordingly, the enzyme has not been practically used because of insufficient reaction specificity, stability, and quantitative availability. Furthermore, a cDNA sequence encoding GalNAc α 2,6-sialyltransferase (EC 2.4.99.3; GalNAc-α 6ST) has not yet been cloned.

Each of the aforementioned sialyltransferases whose structures having been revealed has a hydrophobic segment located at the $NH_2$-terminal region, and is a type II transmembrane protein immobilized to cell membrane by the hydrophobic segment. From this reason, a problem arises that expressed enzymes are immobilized to cell membranes and are not capable of being extracellularly released, where expressions are carried out using vectors containing sialyltransferase genes that are transfected into mammalian cells. Furthermore, another problem may arise, when the expression is performed using mammalian cells, that enzyme expressions may be reduced as endoplasmic enzyme concentrations exceed certain levels.

In order to solve the above problems, an extracellularly releasable fused protein may be prepared which comprises an active domain of a sialyltransferase and a signal peptide region. This method is characterized in that a sialyltransferase can be readily recovered from a cell cultivation mixture, because the method involves the step of extracellular release of the fused protein which retains sialyl transfer activity and function as a sialyltransferase. However, where the expression of a sialyltransferase is performed using a mammalian cell, a transfected cell may be unstable or troublesome cultivation procedures are required. In addition, in order to obtain a large quantity of expressed sialyltransferase, a mass cell culture is essential for a long period of time, which may cause disadvantageous from viewpoints of cost and manufactural installations.

Processes are well known to those skilled in the art to obtain cloned cDNA sequence encoding an enzyme expressed in mammalian cells and prepare a recombinant vector containing a gene encoding the enzyme, per se, or in a soluble form, and to transform microorganisms with the vector. A desired enzyme can be produced, in a large quantity, by culturing the transformant obtained by the aforementioned method to allow the microorganism to express the enzyme, per se, or in a soluble form that has the desired activity.

This process comprises, for example, a step of culturing a transformed microorganism and extracting an expressed enzyme by lysis of the microorganisms using lysozyme or the like. However, a large amount of insoluble or soluble proteins is expressed in the microorganisms in a short period of time, and such proteins may aggregate inside the microorganisms to form proteinic aggregates or precipitates. Accordingly, it is necessary to extract the protein from such aggregates or precipitates.

To extract the desired protein from the aforementioned aggregates or precipitates, generally employed methods are those using urea, guanidine hydrochloride and the like. In this approach, the expressed protein is generally subjected to denaturation using, for example, urea for solubilization (by an exposure of the hydrophobic region), and then to renaturation treatment. The renaturation may be achieved by removing the urea through dialysis. However, for the removal of urea, a problem is that optimal conditions including pH, salt concentration, and temperature must be chosen that are strictly specific to each of the enzymes, and this optimization of conditions is extremely time-consuming. If inappropriate conditions are applied, recovered enzyme may retain almost no activity, and therefore, the selection of the conditions for the renaturation is particularly important.

Accordingly, one object of the present invention is to provide purified GalNAc α 2,6-sialyltransferase. Another object of the present invention is to provide a DNA sequence encoding GalNAc α 2,6-sialyltransferase and an amino acid sequence of the enzyme by cloning a cDNA sequence that encodes GalNAc α 2,6-sialyltransferase. Further objects of the present invention are to provide an extracellularly releasable protein comprising an active domain of the GalNAc α 2,6-sialyltransferase and to provide a process for a mass expression of said protein in microorganisms. It is also an object of the invention to provide a process for extraction of an expressed sialyltransferase from aggregate thereof in microorganisms and a process of efficient renaturation of the extract.

SUMMARY OF THE INVENTION

The present inventors conducted various studies to achieve the foregoing objects, and as a result, they succeeded in cloning the cDNA encoding GalNAc α 2,6-sialyltransferase from chick embryo. The present invention was achieved on the basis of these findings. The present invention thus provides GalNAc α 2,6-sialyltransferase P-B1 characterized by the amino acid sequence disclosed as SEQ ID NO.5 in the sequence listings. The present invention also provides GalNAc α 2,6-sialyltransferase genes encoding the aforementioned amino acid sequence of GalNAc α 2,6-sialyltransferase P-B1, and as an embodiment thereof, a GalNAc α 2,6-sialyltransferase gene characterized by the nucleotide sequence from nucleotide No.1 to 1698 disclosed as SEQ ID NO.1 in the sequence listings. Also provided are recombinant vectors comprising the above GalNAc α 2,6-sialyltransferase gene and plasmid λ CEB-3034 as an embodiment thereof, transformants which are transformed with the above recombinant vector, and the active domain of GalNAc α 2,6-sialyltransferase characterized by the amino acids of No. 233 through 566 of the amino acid sequence disclosed as SEQ ID NO.5 in the sequence listings.

The GalNAc α 2,6-sialyltransferase P-B1 has activity of transferring sialic acid to the 6-position of N-acetylgalactosamine directly bound to a protein regardless of the presence or absence of a substituent on hydroxyl group at the 3-position. The structure of NeuAc α 2,6GalNAc-protein is thus readily formed by the enzyme, which terminates further extension of the resulting sugar chain. Therefore, where a longer sugar chain is desired, a sugar chain synthetic scheme should be designed so that this enzyme can be employed after complete extension of a sugar chain. For this reason, a sialyltransferase is highly useful which fails to transfer sialic acid to an N-acetylgalactosamine that has unsubstituted 3-hydroxyl group and bonded to a protein via an α-glycoside linkage, but can transfer sialic acid to the 6-position of an N-acetylgalactosamine bound to a protein via an α-glycoside linkage, only when the hydroxyl group at 3-position is substituted with a galactose or a sugar chain having a galactose at its reduced terminus.

Therefore, the inventors of the present invention cloned a CDNA from chicken testes that encodes GalNAc α 2,6-sialyltransferase having the aforementioned features, and as a result, they achieved the present invention relating to the GalNAc α 2,6-sialyltransferase P-B3 characterized by the amino acid sequence disclosed as SEQ ID NO.7 in the sequence listings. The present invention thus provides GalNAc α 2,6-sialyltransferase genes encoding the above amino acid sequence of the GalNAc α 2,6-sialyltransferase P-B3, and as an embodiment thereof, the GalNAc α 2,6-sialyltransferae gene having the nucleotide sequence of from nucleotide No.1 to 1212 as disclosed as the SEQ ID NO.3 in the sequence listings. The present invention also provides a recombinant vector comprising the above GalNAc α 2,6-sialyltransferase gene and plasmid λ CEB3-T20 as an embodiment thereof, and a transformant being transformed with the above recombinant vector.

The inventor of the present invention further conducted studies to provide an extracellularly releasable protein comprising a portion, i.e. active domain, that is derived from the structure of the aforementioned GalNAc α 2,6-sialyltransferase and is responsible for its activity. As a result, they succeeded in identifying a partial polypeptide of the above-described GalNAc α 2,6-sialyltransferase as being the active domain, and achieved the present invention directed to an extracellularly releasable protein which comprises the polypeptide region together with a signal peptide and catalyzes GalNAc α 2,6-sialic acid transfer. As an embodiment thereof, protein SB-690 characterized by the amino acid sequence disclosed as SEQ ID NO.6 in the sequence listings. The present invention also provides genes encoding the above protein, and as an embodiment thereof, a gene having the nucleotide sequence characterized by nucleotide No.1 to 1065 disclosed as SEQ ID NO.2 of the sequence listings, and a recombinant vector containing the aforementioned gene and plasmid pcDSB-690 as an embodiment thereof. Further provided are a transformant being transformed with the above recombinant vector and a process for preparing the aforementioned protein which comprises the steps of culturing the above transformant and recovering the above protein from the culture.

In addition, the inventors found that a Gal β 1,4GalNAc α 2,6-sialyltransferase with a highly restored activity can be prepared by expressing mouse Gal β 1,4GalNAc α 2,6-sialyltransferase in an insoluble form in *Escherichia coli*, followed by extracting the enzyme with urea and subjecting the enzyme to renaturation under optimal conditions, and thus achieved the present invention. In accordance with the present invention, there is provided a process for producing a sialyltransferase which comprises the steps of: (a) expressing a sialyltransferase in a microorganism; (b) extracting the sialyltransferase with about 5 to 9M urea from proteinic aggregates or precipitates accumulated inside the microorganism and containing the enzyme; (c) diluting the extract obtained by the above step (b) with a renaturation composition to obtain a primary dilution containing about 1 to 4M urea; (d) diluting the primary dilution obtained by the above step (c) with a renaturation composition to obtain a secondary dilution containing about 0.5 to 2M urea; and (e) removing urea from the secondary dilution obtained by the above step (d) by dialysis to afford a renatured sialyltransferase.

BRIEF DESCRIPTION OF THE DRAWINGS

FIG. 4 shows the result of comparison between the primary sequences of GalNAc α 2,6-sialyltransferase P-B3 and GalNAc α 2,6-sialyltransferase P-B1 according to the present invention. In the figure, amino acids are represented by the one-letter abbreviations.

DESCRIPTION OF THE PREFERRED EMBODIMENTS

Figure 1:
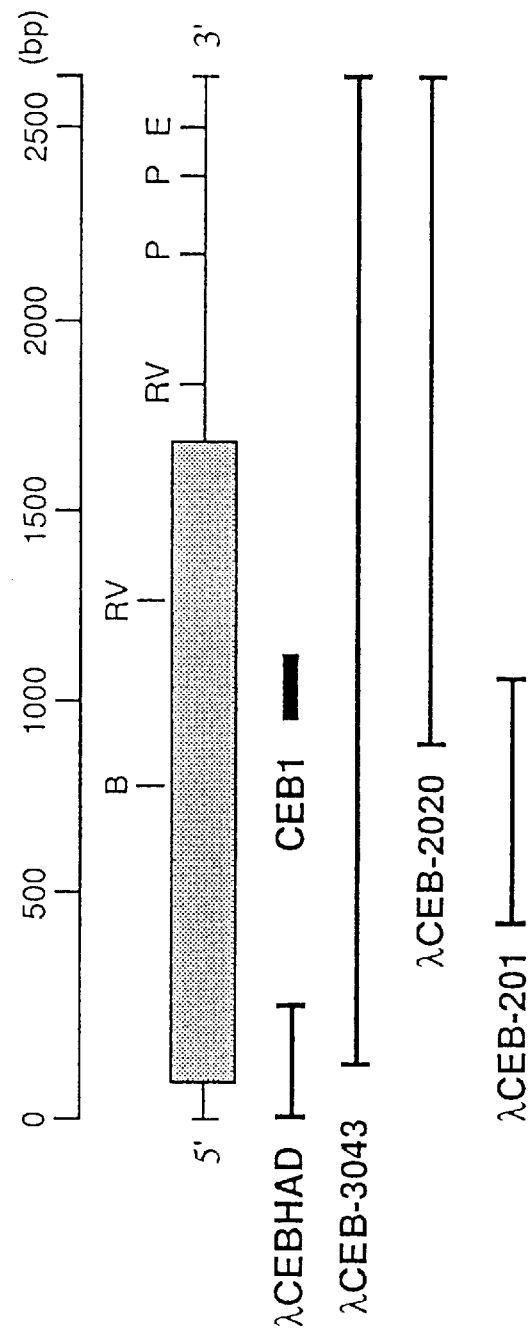
FIG. 1 shows a restriction map of the cDNA clone encoding GalNAc α 2,6-sialyltransferase P-B1. In the figure, E represents EcoRI; RV: EcoRV; P: PstI; and B: BglII.

As the most preferred embodiments of the present GalNAc α 2,6-sialyltransferases, GalNAc α 2,6-sialyltransferases P-B1 and P-B3 are provided. The explanations set out below will detail GalNAc α 2,6-sialyltransferases P-B1 and P-B3 as examples of the enzyme of the present invention. However, the GalNAc α 2,6-sialyltransferases of the present invention are not limited to the GalNAc α 2,6-sialyltransferase P-B1 or P-B3. GalNAc α 2,6-sialyltransferases comprising the active domain of the GalNAc α 2,6-sialyltransferase P-B1 and/or that of P-B3, both were first revealed by the present invention, or alternatively, those comprising one or more active domains of the GalNAc α 2,6-sialyltransferase in which the aforementioned acid sequence is partially changed or modified also fall within the scope of the present invention. A preferred example of such active domains as mentioned above is the active domain of the GalNAc α 2,6-sialyltransferase characterized by amino acids No.233 to 566 of the amino acid sequence disclosed as SEQ ID NO.5 of the sequence listings.

The methods for isolation of the respective cDNAs encoding GalNAc α 2,6-sialyltransferase P-B1 and GalNAc α 2,6-sialyltransferase P-B3 will be detailed in Examples set out below. However, the methods for isolation of the cDNAs encoding GalNAc α 2,6-sialyltransferase P-B1 and GalNAc α 2,6-sialyltransferase P-B3 are not limited to those methods. One of ordinarily skilled artisan can readily isolate the desired cDNAs by referring to the methods described in the following examples, or alternatively, by appropriately modifying or altering those methods. In addition, the nucleotide sequences disclosed as SEQ ID Nos.1 through 3 in the sequence listings may be synthetically prepared and used to carry out the present invention.

The DNA sequence encoding GalNAc α 2,6-sialyltransferase P-B1 as defined by SEQ ID No.1 in the sequence listings and the DNA sequence encoding GalNAc α 2,6-sialyltransferase P-B3 as defined by SEQ ID No.3 are the preferred embodiments of the present invention. However, the DNA sequences encoding GalNAc α 2,6-sialyltransferase P-B1 or GalNAc α 2,6-sialyltransferase P-B3 of the present invention are not limited to those specified embodiments, and any one of DNA sequences encoding the respective amino acid sequences of GalNAc α 2,6-sialyltransferase P-B1 and GalNAc α 2,6-sialyltransferase P-B3 revealed by the present invention fall within the scope of the present invention. For example, the DNA sequence encoding the active domain of GalNAc α 2,6-sialyltransferase characterized by the amino acids of from No. 233 to 566 of the amino acid sequence as defined by SEQ ID No.5 in the sequence listings is a preferred embodiment of the present invention. In addition, the DNA characterized by the nucleotides sequence of from nucleotide No. 699 to 1698 of the SEQ ID No.1 shown in the sequence listings is a particularly preferred embodiment of the present invention.

The GalNAc α 2,6-sialyltransferases of the present invention, including P-B1 and P-B3 for example, may occasionally be retained inside the cells after expression and not released extracellularly. Furthermore, when endoplasmic concentrations of the enzymes exceed certain levels, expressed amounts of the enzymes may possibly be reduced. In order to efficiently utilize the aforementioned GalNAc α 2,6-sialic acid transfer activities of GalNAc α 2,6-sialyltransferase P-B1 and P-B3, proteins in soluble forms may be prepared in which the activities of these enzymes are retained and can be released extracellularly from cells upon their expressions. Examples of such proteins include, for example, extracellularly releasable proteins which comprise a polypeptide, as being an active domain of the above-described GalNAc α 2,6-sialyltransferase P-B1 or P-B3 and is responsible for the GalNAc α 2,6-sialyltransferase activity, and catalyze the GalNAc α 2,6-sialic acid transfer.

The sialyltransferases so far cloned have domain structures similar to those of other glycosyltransferases: a short $NH_2$-terminal cytoplasmic tail; a hydrophobic signal-anchor domain; a proteolytically sensitive stem region; and a large COOH-terminal active domain (Paulson, J. C. and Colley, K. J., J. Biol. Chem., 264, 17615–17618, 1989). To determine the location of the transmembrane domain of the GalNAc α 2,6-sialyltransferase P-B1 of the present invention, hydropathy plot may be used which can be prepared according to the method of Kyte and Doolittle (Kyte, J. and Doolittle, R. F., J. Mol. Biol., 157, 105–132, 1982). To evaluate a putative active domain, recombinant plasmids introduced with various fragments may be produced and utilized. Exemplary methods will be de tailed in the Examples set out below. However, the methods for determination of the location of the transmembrane domain or evaluation of a putative active domain are not limited to the disclosed methods.

For the preparation of the extracellularly releasable protein comprising a polypeptide portion, as being an active domain of the above-described GalNAc α 2,6-sialyltransferase P-B1 or P-B3, together with a signal peptide, an immunoglobulin signal peptide sequence, for example, may be used as the signal peptide, and a sequence corresponding to the active domain of GalNAc α 2,6-sialyltransferase P-B1 or P-B3 may be fused in-frame to the signal peptide. For example, the method of Jobling et al. (Jobling, S. A. and Gehrke, L., Nature (Lond.), 325, 622–625, 1987) may be applied as such methods, whose specified procedure will be detailed in the Examples of the present specification with respect to GalNAc α 2,6-sialyltransferase P-B1. However, types of the signal peptide and methods for ligation of the signal peptide and the active domain are not limited to the aforementioned methods, and a person skilled in the art can suitably choose the polypeptide portion as being an active domain of GalNAc α 2,6-sialyltransferase, preferably GalNAc α 2,6-sialyltransferase P-B1 or P-B3, and produce the extracellularly releasable protein by ligating the polypeptide portion to any available signal peptide according to an appropriate method. The most preferred example of these proteins is protein SB-690 of the present invention.

According to another embodiment of the present invention, there is provided a process for producing a sialyltransferase which comprises the steps of: (a) expressing a sialyltransferase in a microorganism; (b) extracting the sialyltransferase with about 5 to 9M urea from proteinic aggregate or precipitate containing the enzyme and being accumulated inside the microorganism; (c) diluting the extract obtained by the above step (b) with a renaturation composition to obtain a primary dilution containing about 1 to 4M urea; (d) diluting the primary dilution obtained by the above step (c) with a renaturation composition to obtain a secondary dilution containing about 0.5 to 2M urea; and (e) removing urea from the secondary dilution obtained by the above step (d) by dialysis to afford a renatured sialyltransferase. As described above, sialyltransferases share the common domain structure, and therefore, the preparation process of the present invention may be applicable to any type of sialyltransferase. For example, GalNAc α 2,6-sialyltransferase or Gal β 1,4GalNAc α 2,6-sialyltransferase of the present invention can be suitably prepared by the process of the present invention.

According to an embodiment of the process of the present invention, 8M urea is used in the step (b); a primary dilution containing about 2 to 3M urea is obtained in the step (c); a secondary dilution containing about 1 to 2M urea is obtained in the step (d); and the secondary dilution is dialyzed in the presence of divalent cations in the step (e). According to another embodiment of the present method, 8M urea is used in the step (b); a primary dilution containing about 2 to 3M urea is obtained by being left stand for 12 hours or more at 4° C. after primary dilution in the step (c); a secondary dilution containing about 1 to 2M urea is obtained by being left stand for 48 hours or more after secondary dilution in the step (d); and the secondary dilution is dialyzed in the presence of divalent cations in the step (e). In addition, it is also a preferred method in which the renaturation composition used in the step (c) contains 1 to 2M urea, 20 mM MOPS-NaOH, 0.5M NaCl, 20 mM lactose, 0.5 mM EDTA (pH 7.0) and the renaturation composition used in the step (d) contains 20 mM MOPS-NaOH, 0.5M NaCl, 20 mM lactose, 0.5 mM EDTA (pH 7.0).

The first step of the process for the preparation of sialyltransferase according to the present invention is the expression of a sialyltransferase in microorganisms. To this end, previously cloned genes of sialyltransferases can be used. As cDNAs encoding sialyltransferases, the cDNA encoding Gal β 1,4GlcNAc α 2,6-sialyltransferase (Gal β 4GlcNAc-α 6ST, see, Weinstein et al., Grundmann et al., Bast et al. and Hamamoto et al., supra), the cDNA encoding Gal β 1,3(4)GlcNAc α 2,3-sialyltransferase (Gal β 3(4)GlcNAc-α 3ST, see, Wen et al. and Kitagawa et al., supra), the cDNA encoding Gal β 1,3GalNAc/Gal β 1,4GlcNAc α 2,3-sialyltransferase (see, Sasaki et al., supra), the cDNA encoding Gal β 1,3GalNAc α 2,3-sialyltransferase (Gal β 3GalNAc-α 3ST, see, Gillespie et al. and Japanese Patent Unexamined Publication No. 5-504678/1993; and Lee et al., supra), for example, may be used, as well as cDNAs encoding the GalNAc α 2,6-sialyltransferases of the present invention. Sialyltransferase genes contained in these nucleotide sequences, per se, may be used for the expression of the naturally-derived enzymes.

According to the present invention, in addition to the naturally-derived sialyltransferases mentioned above, non-natural sialyltransferases in which the polypeptide sequences of the naturally-derived sialyltransferases are partly deleted or modified may be expressed in microorganisms. For example, since sialyltransferases have a hydrophobic segment (transmembrane domain) in the $NH_2$-terminal region, and sialyltransferases in soluble forms wherein the hydrophobic segment is deleted are preferably expressed in the microorganisms. In addition, deletion of both of the hydrophobic segment and the cytosol segment is also preferred.

In order to produce recombinant vectors for the expression of sialyltransferases, the entire sequences or partial regions of the genes of naturally derived sialyltransferases may be selectively amplified by, for example, PCR method. For example, a sialyltransferase gene (a PCR fragment) may be readily prepared which has an initiation codon and a cloning site and lacks the cytosol domain and transmembrane domain. This type of sialyltransferase genes are suitably used for the introductions into vectors for microbial expressions due to the presence of the initiation codon and the cloning site. In addition, said genes are preferred since they encode non-natural sialyltransferases, in which a part of the polypeptide sequence of the naturally-derived sialyltransferase is deleted, and express non-natural soluble sialyltransferase in microorganisms.

According to the process of the present invention, microorganisms such as *Escherichia coli* may be used for the expression of sialyltransferase. A microbial expression vector suitably used for transformation of such microorganisms may be suitably selected by an ordinarily skilled artisan. For example, where *E. coli* JM109(DE3) or the like is used as the microorganism, microbial expression vectors such as pET3b (Studier, F. W. et al., Method. Enzymol., 185, pp.60–89, 1990) may be used. Methods for introducing the above described sialyltransferase genes into microbial expression vectors and methods for transforming microorganisms with recombinant vectors are both well known to those skilled in the art.

The transformants can be cultured according to methods for culturing transformed microorganisms well known to those skilled in the art. For efficient expression of a desired sialyltransferase in microbial cells, replication of the recombinant protein can be initiated by, for example, the induction of T7-RNA polymerase during the logarithmic growth phase of the transformants. A large amount of naturally-derived or non-natural sialyltransferase is expressed inside the transformants thus obtained, which generally forms proteinic aggregate or precipitate.

The second step of the process of the present invention is the extraction step of a sialyltransferase with 5 to 10M urea from the proteinic aggregate or precipitate which is accumulated inside the cells and contains the sialyltransferase. In order to expose the proteinic aggregate or precipitate to outside of the microorganisms for its separation, the cultured transformants can be treated with, for example, lysozyme or Triton X-100 and then insoluble fractions may be collected by centrifugation. After then, the precipitates are suspended in a buffer (for example, 10 mM Tris-HCl, pH 7.4) at a protein concentration of about 1 to 10 mg/ml and are subjected to extraction with urea.

For example, solid urea is added to the suspension so as to be 5 to 10M, preferably 8M of final concentration, and the precipitates are subjected to extraction for 15 minutes to 2 hours, preferably 30 minutes at 4° to 25° C., preferably at 10° C. While not bound by any specific theory, the hydrophobic portion of a sialyltransferase contained in the extract is exposed by the action of urea, and as a result, a solubilized sialyltransferase is extracted from the proteinic aggregates or precipitates.

Then, an extract solution containing a denatured sialyltransferase can be obtained by removing the precipitates by, for example, centrifugation of the extract at 12,000×g for 15 minutes. This extract normally contains about 0.5 mg/ml of proteins. For example, when 5.7M urea is used for the extraction, about 80% of proteins can be recovered. Furthermore, upon the extraction, NaCl and Tris-HCl (pH 7.4) are preferably added so that their final concentrations of 0.3M and 20 mM, respectively, are achieved. Exemplary procedure of the extraction will be explained in detail in the Examples set out below.

The sialyltransferase contained in the extract exposes hydrophobic portions and its higher-order structure is damaged. According to the process of the present invention, renaturation of the sialyltransferase contained in the extract is performed as the third step. The term renaturation herein used means restoration of the higher-order structure of the protein that is lost during the extraction step and the entire or partial recovery of the enzymatic activity. This step is characterized in that the extract is diluted stepwise with a renaturation composition so that the urea concentration can be gradually lowered to efficiently achieve the renaturation of the sialyltransferase.

The renaturation process comprises the steps of, for example, diluting the extract with a renaturation composition to obtain a primary dilution containing about 1 to 4M urea; diluting the primary dilution with a renaturation composition to obtain a secondary dilution containing about 0.5 to 2M urea; and removing the urea from the secondary dilution by dialysis to afford a renatured sialyltransferase.

A preferred embodiment of the process comprises the steps of, for example, diluting the extract with a renaturation composition to obtain a primary dilution containing about 2 to 3M urea; diluting the primary dilution with a renaturation composition to obtain a secondary dilution containing about 1 to 2M urea; and removing the urea from the secondary dilution by dialysis in the presence of one or more divalent cations to afford a renatured sialyltransferase. A further preferred embodiment is a process comprises the steps of, for example, diluting the extract with a renaturation composition and the result is allowed to stand for 12 hours or more at 4° C. to obtain a primary dilution containing about 2 to 3M urea; diluting the primary dilution with a renaturation composition and the result is allowed to stand for 48 hours or more to obtain a secondary dilution containing about 1 to 2M urea; and removing the urea from the secondary dilution by dialysis in the presence of one or more divalent cations to afford a renatured sialyltransferase.

As the renaturation composition, for example, 2M urea, 20 mM MOPS-NaOH (MOPS: 3-morpholinopropanesulfonic acid) (pH 7.0), 0.5M NaCl, 10 mM lactose, 0.5 mM EDTA; and 2M urea, 20 mM Tris-HCl, 0.3M NaCl, 20 mM lactose, 0.5 mM EDTA (pH 7.4) may be used. In addition, a modified composition may be used in which the components of the latter composition may be changed to, for instance, 20 mM Tris-HCl (pH 8.0); 20 mM MOPS-NaOH (pH 7.0); 20 mM MES-NaOH (pH 6.0) (MES: 3-morpholinoethanesulfonic acid); 0.5M NaCl; 0.1M NaCl; or 1M urea. Furthermore, compositions not containing urea or lactose may also be used. Among these, 2M urea, 20 mM MOPS-NaOH, 0.5M NaCl, 20 mM lactose, 0.5 mM EDTA (pH 7.0) is preferably used. When the concentration of NaCl is below 0.1M, or pH exceeds 9, renaturation efficiency is undesirably reduced. Generally, a salt concentration of 0.3 to 0.5M and pH of 6 to 8 are preferred after the addition of the renaturation composition.

The first dilution comprises the step of preparing a primary dilution using the aforementioned renaturation composition so that a final protein concentration of the extract is 0.01 to 0.05 mg/ml, preferably about 0.02 mg/ml. For example, the extract may be diluted 10 to 40-fold, preferably about 20-fold, and a urea concentration may be 1 to 4M, preferably not higher than about 3M and not lower than about 2M. Dilution treatment is generally and preferably performed at 4° C. This primary dilution mixture is left stand for 12 hours or more at 4° C., most preferably for about 12 hours, to initiate gradual renaturation.

The secondary dilution is carried out by diluting the primary dilution with an equal volume of renaturation composition, preferably not containing urea, to achieve approximately the half urea concentration. Through this dilution, urea concentration of the secondary dilution should be lowered to about 0.5 to 2M, preferably not higher than about 2M and not lower than 1M (e.g., 1 to 2M), and most preferably at about 1.2M. The secondary dilution is allowed to stand for 40 hours to 2 weeks, preferably 48 to 72 hours, most preferably about 48 hours at 4° C., to proceed gradual renaturation.

After then, to achieve perfect renaturation, the above obtained secondary dilution is dialyzed against, for example, a renaturation composition free from urea to completely remove remaining urea. The dialysis may be carried out at 4° C. for about 48 hours. Dialysis solution may be, for example, any one of buffer solutions in which the sialyltransferase can be stored stably, as well as the renaturation composition.

In addition, by carrying out the primary and secondary dilution and the final dialysis in the presence of one or more divalent cations, renaturation efficiency can be further improved. Examples of the divalent cations include, for example, magnesium ions and manganese ions. These ions may be used at a concentration of 1 to 10 mM, preferably about 5 mM. It is particularly preferred that the dialysis is performed in the presence of one or more divalent cations. When a reducing agent such as dithiothreitol and mercaptoethanol is added before complete removal of urea in the final dialysis step, the enzymatic activity may occasionally be lost. However, after the urea is completely removed, the enzyme restores resistance to the reducing agent to exhibit the sialyltransferase activity.

The present invention will be further explained more specifically by referring to the following examples. However, the scope of the present invention is not limited to these examples.

EXAMPLES (A) Preparation of GalNAc α 2,6-sialyltransferase P-B1

In order to obtain a cDNA clone of GalNAc α 2,6-sialyltransferase P-B1, PCR with two degenerate oligonucleotides (ST-107 and ST-205) was performed using chick embryo cDNA as a template. A fragment of the desired size of approximately 150 bp was obtained. Among the PCR recombinants, one clone, designated as CEB1, was found to have an unique amino acid sequence distinct from the known sialylmotifs of Gal β 4GlcNAc-α 6STRL (residues 180–225), Gal β 3(4)GlcNAc-α 3STRL (residues 158–203), and Gal β 3GalNAc-α 3STPS (residues 144–189). The homologies of the sialylmotif of CEB1 with those of Gal β 4GlcNAc-α 6STRL, Gal β 3(4)GlcNAc-α 3STRL and Gal β 3GalNAc-α 3STPS were 56%, 58% and 60%, respectively.

Screening of a 6-day-old chick embryo cDNA library with the cDNA insert from the CEB1 was carried out, and as a result, several cDNA clones were identified. Among them, clone λ CEB-3043 contained a 2.7 kb insert (FIG. 1). To obtain other overlapping clones, a random-primerd cDNA library was again screened by hybridization with the 0.8 kb EcoRI-BglII fragment of the 5'-end of the λ CEB-3043. Fifteen clones were isolated from the cDNA library. Among them, one clone, λ CEBHAD contained a 220 bp insert overlapping with the 5'-end of clone λ CEB-3043 for 160 bp.

The combined DNA from these two cDNAs contained a 1.7 kb of open reading frame that ends at a TGA terminal codon at nucleotide 1699. A poly adenylation signal (AATAAA) at 23 nucleotides upstream from the poly(A) sequence exists at the 3'-end. Translation of this open reading frame affords GalNAc α 2,6-sialyltransferase P-B1 of the present invention (occasionally referred to as P-B1 in the examples) of 566 amino acids with a molecular mass of 64,781, which starts with a methionine codon at nucleotide 1 with a conventional initiation sequence (Kozak, M., Nature (Lond.), 308, 241–246, 1984). The cDNA including a gene encoding the GalNAc α 2,6-sialyltransferase of the present invention, the nucleotide sequence of λ CEB-3043 as being the gene encoding the GalNAc α 2,6-sialyltransferase of the present invention, and the amino acid sequence of the GalNAc α 2,6-sialyltransferase P-B1 of the present invention are shown in the SEQ ID No.1 and 5, respectively of the sequence listings.

Polymerase chain reaction (PCR)

PCR was performed using degenerate primers [5' primer ST107: TGGGCCTTGGII(A/C)AGGTGTGCTGTTG, and 3' primer ST205: AGGCGAATGGTAGTTTTTG(A/T)GCCCACATC] deduced from conserved regions in Gal β 4GlcNAc-α 6STRL (Weinstein, J. et al., J. Biol. Chem., 262, 17735–17743, 1987), Gal β 4GlcNAc-α 6STHP (Grundmann, U. et al., Nucleic Acids Res., 18, 667, 1990), and Gal β 3GalNAc-α 3STPS (Gillespie, W. et al., J. Biol. Chem., 267, 21004–21010, 1992). To obtain cDNA, poly (A)-rich RNA (2 μg) from 3 day-old chick embryos was incubated with an oligo-dT primer (Pharmacia), 1 mM each of dATP, dCTP, dGTP and dTTP, and 2 U/μl of RNase inhibitor (Promega) in 10 mM Tris-HCl (pH 8.3), 50 mM KCl 1.5 mM MgCl$_2$ and 0.001% gelatin in 50 μl for 10 min at 0° C., and then for further incubation was carried out for 60 min at 42° C. after the addition of 100 μU Moloney murine leukemia virus reverse transcriptase (BRL).

After heating the reaction mixture at 94° C. for 3 min, cDNA prepared from 0.2 μg of poly(A)-rich RNA was used for the PCR experiment in a mixture comprising 10 mM Tris-HCl (pH 8.3), 50 mM KCl, 1.25 mM MgCl$_2$ 0.001% gelatin, 200 μM of each dATP, dCTP, dGTP and dTTP, 2 U of Taq DNA polymerase (Promega), and 40 pmoles of each PCR primer in 50 μl. PCR amplification, 35 cycles, was carried out, each cycle consisting of denaturation at 96° C. for 45 sec, annealing at 50° C. for 60 sec, and extension at 72° C. for 60 sec. The PCR products were developed on a 3% agarose gel. The DNA fragment corresponding to 150 bp was eluted from the gel (Qiaex kit; Qiagen), blunt-ended and kinated, and then subcloned into the SmaI site of pUC119, and finally sequenced.

Construction of a cDNA library

Total RNA was prepared from chick embryos (6-day-old) by the guanidinium thiocyanate method, followed by centrifugation in a 5.7M CsCl solution (Sambrook, J., Molecular Cloning: a Laboratory Manual, 2nd ed. Cold Spring Harbor Laboratory, Cold Spring Harbor, N.Y. 1989). Poly (A)-rich RNA was purified with oligotex-dT30 (Takara), and then employed for the construction of a cDNA library using λ ZAPII (Stratagene) and cDNA synthesis (Pharmacia) kits with an oligo-dT primer and random primers.

Screening of the cDNA library

The amplified cDNA library (1×10$^6$ plaques) was screened with the chick embryo PCR fragments. The plaque-transferred filters were hybridized with $^{32}$P-radiolabeled DNA probes for 12 h at 65° C. in 5× SSC, 0.02% SDS, 5× Denhardt's solution and 10 μg/ml denatured salmon sperm DNA, and then washed twice at 65° C. for 20 min in 2× SSC, 0.1% SDS. To obtain plasmids from the isolated phage clones, phagemid rescue was performed according to the manual of the manufacturer of the λ ZAPII cloning kit (Stratagene). cDNA inserts were excised directly as Bluescript plasmids. Plasmids were produced by the standard molecular cloning method according to Sambrook et al. (Sambrook, J. et al., Molecular Cloning: a Laboratory Manual).

DNA sequence analysis

The DNA sequences of the inserts were determined by the dideoxy-chain termination method (Sanger, F. et al., Proc. Natl. Acad. Sci. USA, 74, 5463–5467, 1977) using single-strand DNA as a template for T7-DNA polymerase. The sequencing reaction and electrophoresis were carried out using the AutoRead DNA sequencing kit and a DNA sequencer (Pharmacia). Single strand DNA was prepared from *Escherichia coli* XL-Blue (Stratagene) after superinfection with helper phage R408 (Stratagene). The sequence data were analyzed with a computer using PC/Gene (Teijin System Technology).

Northern and Southern blot analyses

To confirm the existence of the gene, Southern blot analysis of chick genomic DNA was performed. Hybridization with the EcoRI cDNA insert of λ CEB-201 gave a single band for the DNA digested with EcoRI and BamHI, and two bands for the DNA digested with HindIII and SacI. This simple hybridization pattern indicates that the cloned cDNA is a single copy gene.

The transcription pattern during embryonic development was examined by Northern blot hybridization. Analysis of RNA from 6, 8 and 10 day-old chick embryos revealed two RNA species of 3.0 and 2.2 kb. The 3.0 kb transcript was abundant and constantly expressed during all embryonal stages. A low level of the 2.2 kb transcript was detected in 6 day-old embryos and its expression was decreased in 8 and 10 day-old embryos. The gene expression was analyzed using 10 μg poly(A)-rich RNA obtained from various chicken tissues: brain, heart, liver, lung, kidney, and testis. Very low levels of the 3.0 and the 4.0 kb transcripts was detected in testes, while almost no signals were detected in other tissues. The following description details each of the experiments.

For Northern blots, 5 μg of denatured poly(A)-rich RNAs from chick embryo was size-fractionated on formaldehyde-agarose gels and then blotted onto Hybond N+ nylon membranes (Amersham). For Southern blots, 7.5 μg of genomic DNA prepared from chick embryos was digested with restriction enzymes EcoRI, BamHI, HindIII and SacI, and then size-fractionated on 0.6% agarose gels. After electrophoresis, the gels were denatured (30 min) in 0.5N NaOH and 1.5M NaCl and neutralized (30 min) in 0.5M Tris-HCl (pH 7.5) and 1.5M NaCl, and then the DNA was transferred onto Hybond N+ nylon membranes. Both Northern and Southern filters were prehybridized in 50% formamide, 5× SSC, 5× Denhardt's, 0.5% SDS, and 10 μg/ml denatured salmon sperm DNA at 37° C. for 1 h, and then hybridized with a $^{32}$P-labelled DNA probe for 12 h under the same conditions as for prehybridization. The probe applied was a 0.6 kb EcoRI cDNA insert of λ CEB-201, which was labeled with a Multiprime Labeling System (Amersham). The filters were washed twice for 10 min at 65° C. in 2× SSC and 0.1% SDS, followed by washing twice with 0.2× SSC and 0.1% SDS at 65° C. for 30 min, and then exposed to Kodak XAR film for about one day at −70° C.

The amino acid sequence of the sialyltransferase P-B1 of the invention, which was revealed as described above, shows the following characteristic features that are not observed in sialyltransferases so far known.

(i) All of the sialyltransferases previously cloned are critical Type II membrane proteins. They have a domain structure similar to that of other glycosyl-transferases: a short $NH_2$-terminal cytoplasmic tail; a hydrophobic signal-anchor domain; a proteolytically sensitive stem region; and a large COOH-terminal active domain. On the other hand, the sialyltransferase P-B1 of the invention has a large stem region (or intermediate region).

(ii) The sialyltransferase P-B1 of the invention has a PEST region (residues 233–258). It has been known that the amino acid sequences of proteins with intracellular half-lives of less than 2 hours contain one or more regions that are rich in proline, glutamic acid, serine, and threonine residues (referred to as PEST: Rogers, S. et al., Science, 234, 364–368, 1986). These PEST regions are generally flanked by clusters containing several positively charged amino acids. Other sialyltransferases previously known do not have this region.

(iii) Two stretches of eight amino acids (SSSXVSTC) were found at residues 247–254 and 330–337. A search of the Genebank database for other proteins revealed no sequence similarity to this sequence.

Sialyltransferases so far known exhibit remarkable tissue-specific expression, which seems to be correlated with the existence of cell type-specific carbohydrate structures (Paulson, J. C. and Colley, K. J., J. Biol. Chem., 264, pp.17615–17618, 1989). The results of Northern blotting indicates that the pattern of expression of sialyltransferase P-B1 apparently changes. The transcriptions of three different sizes of mRNAs (4.0, 3.0 and 2.2 kb) from the sialyltransferase P-B1 gene suggests that they are generated through alternative splicing and alternative promoter utilization mechanisms as observed for Gal β 1,4GlcNAc α 2,6-sialyltransferase (Gal β 4GlcNAc-α 6STRL) and Gal β 1,3(4)GlcNAc α 2,3-sialyltransferases (Gal β 3(4) GlcNAc-α 3STRL, Weinstein, J. et al., J. Biol. Chem., 262, 17735–17743, 1987; and Wen, D. X. et al., J. Biol. Chem., 267, 21011–21019, 1992). This hypothesis is supported by the results of Southern hybridization, which showed the existence of a single copy gene for sialyltransferase P-B1.

(B) Preparation of the soluble form protein SB-690

In order to utilize the GalNAc α 2,6-sialyltransfer activity of the GalNAc α 2,6-sialyltransferase P-B1 of the present invention, protein SB-690 in a soluble form was prepared which retains the activity of the present enzyme and is released from the cells upon expression.

Figure 2:
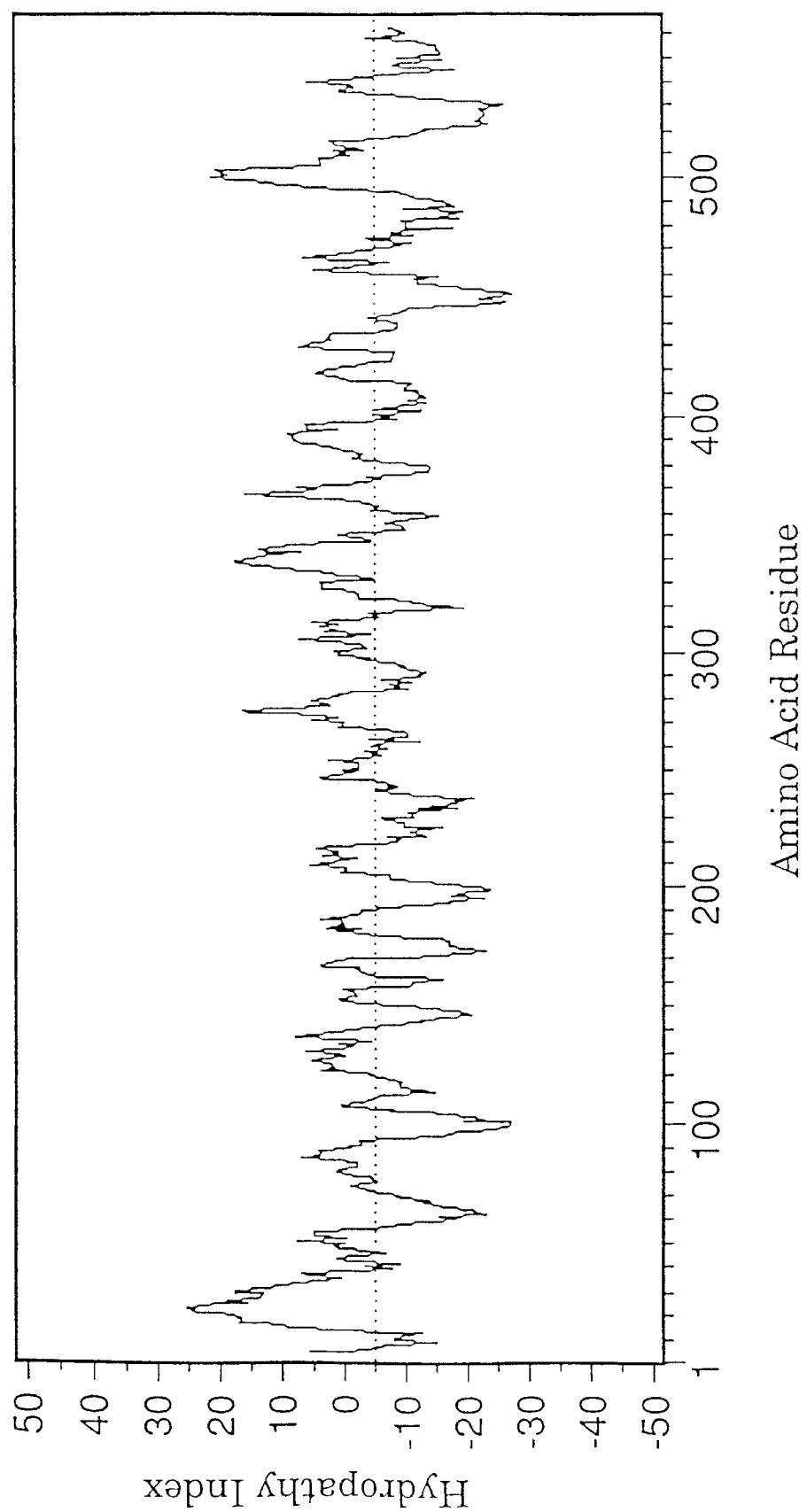
FIG. 2 shows the result of hydrophobicity analysis of the GalNAc α 2,6-sialyltransferase P-B1 according to the present invention. In the figure, N-terminus of the protein is depicted at the left side and positive values indicate hydrophobic regions.

The sialyltransferases so far cloned have a domain structure similar to that of other glycosyl-transferases: a short $NH_2$-terminal cytoplasmic tail; a hydrophobic signal-anchor domain; a proteolytically sensitive stem region; and a large COOH-terminal active domain. To determine the location of any transmembrane domain of GalNAc α 2,6-sialyltransferase of the present invention, a hydropathy plot (FIG. 2) was prepared from the translated sequence according to the method of Kyte and Doolittle (Kyte, J. and Doolittle, R. F., J. Mol. Biol., 157, 105–132, 1982). As as result, it is suggested that a critical hydrophobic transmembrane domain of GalNAc α 2,6-sialyltransferase P-B1 of the present invention consists of 21 amino acid residues from the amino acids No.17 to 37.

Figure 3:
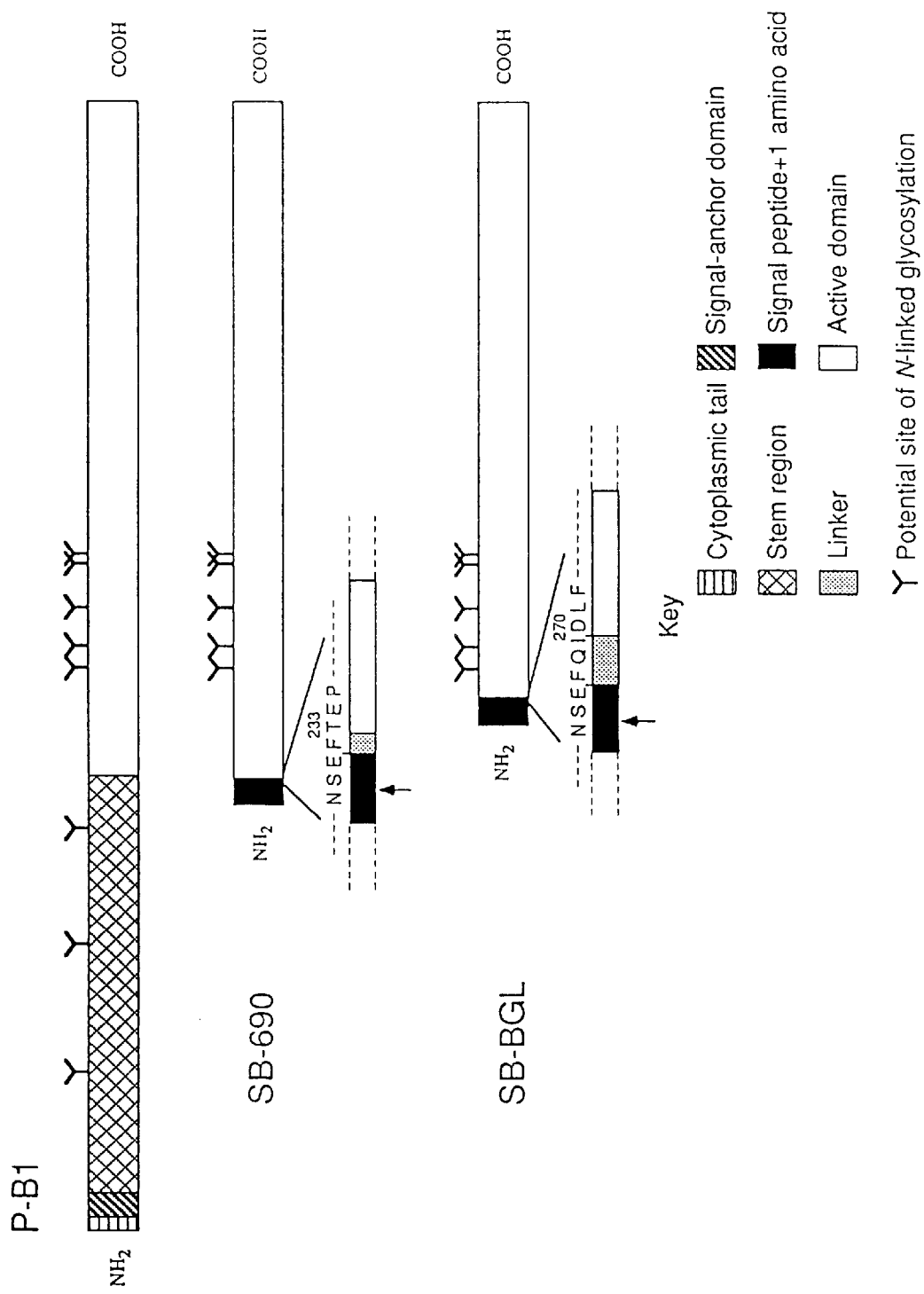
FIG. 3 shows the location of the active domain of the GalNAc α 2,6-sialyltransferase P-B1 according to the present invention and the result of comparison with the structure of protein SB-690 which has GalNAc α 2,6-sialyltransferase activity and can be extracellularly released. In the figure, protein SB-BGL is a protein not having GalNAc α 2,6-sialyltransferase activity.

As described above, the hydrophobic signal anchor domain of GalNAc α 2,6-sialyltransferase is located from amino acid residues No.17 to 37. Residues from 233 to 269 apparently contain certain essential residues for enzymatic activity, because the media from cells transfected with pcDSB-BGL had no significant activity, while the protein (33 KDa) was synthesized in an in vitro translation/transcription system with pSB-BGL as a template. The active domain was thus deduced to be around 233–566 (FIG. 3), which is a comparative size to that of other cloned sialyltransferases. In order to produce the soluble protein containing the active domain described above, the sequence relating to the putative active domain of P-B1 was in-frame fused to the sequence of immunoglobulin signal peptide (Jobling, S. A. and Gehrke. L., Nature (Lond.), 325, 622–625, 1987). Details of the experiments are shown below.

A vector plasmid PUGS was constructed by replacing the PstI-XhoI fragment of the p Bluescript SK(+) plasmid with a 117 bp of a synthetic DNA fragment. This fragment contains 43 bp of the 5'-untranslated leader sequence of Alfalfa Mosaic Virus (Jobling, S. A. and Gehrke, L., Nature (Lond.) 325, 622–625, 1987) with a synthetic PstI site at the 5'-end, followed by the mouse immunoglobulin M heavy chain signal peptide sequence (57 bp) (Boersch-Supan, M. E. et al., J. Exp. Med. 161, 1272–1292, 1985) with a 17 bp of a synthetic EcoRI, BGlII and XhoI cloning site at the 3'-end. The nucleotide sequence of this fragment is 5'-CTGCAGGGTTTTTATTTTTAATTTTCTTTCAAATA CTTCCACCATGAAATTCAGCTGGGTCAT-GTTCTTCCTGATGGCAGTGGTTA-CAGGGGTCAATTCAGAA TTCCAGATCTCGAG-3'.

λ CEB-3043 encoding GalNAc α 2,6-sialyltransferase of the present invention was partially digested with EcoRV, and 1.8 kb fragment was subcloned into EcoRV site of pBluescript SK(+) to generate pCEB-1800. This clone lacks 0.8 kb of 3'-untranslated region of λ CEB-3043. An active domain of GalNAc α 2,6-sialyltransferase P-B1 was generated by PCR using the 5'-primer, 5'-AGGGCTGCTGAATT CACTGAGCCACAG-3' (nucleotides 679–708), with a synthetic EcoRI site at the middle of the primer and a 3' universal M13 sequencing primer and pCEB-1800 as a template. The PCR product was digested with EcoRI and XhoI, and then ligated into the EcoRI/XhoI site of PUGS to yield the plasmid pSB-690. In this plasmid, a sequence obtained by in-frame fusion of the 3'-end of the immunoglobulin signal sequence to the putative active domain of GalNAc α 2,6-sialyltransferase P-B1 was contained. The fusion fragment was excised from pSB-690 with PstI and XhoI, and then inserted into the PstI/XhoI site of expression vector pcDSR α to yield pcDSB-690.

As a control, protein SB-BGL which lacks the active domain of GalNAc α 2,6-sialyltransferase was produced as described below. pCEB-1800 and pUGS were digested with BglII, and the protruding ends were filled by using the Klenow fragment of DNA polymerase. After heat denaturation of the Klenow fragment of DNA polymerase (at 94° C. for 20 min), these plasmids were digested with XhoI. The 1.0 kb fragment from pCEB-1800 was gel purified and subcloned into the blunt-ended BglII/XhoI site of PUGS to yield PSB-BGL. The PstI/XhoI fragment from PSB-BGL was subcloned into the PstI/XhoI site of pcDSR α to generate pcDSB-BGL.

Expression of the above described protein was performed as follows. COS-7 cells were transiently transfected with 5 μg of plasmid DNA using the DEAE-dextran method (McCutchan, J. H. and Pagano, J. S. J. Natl. Cancer Inst. 41, pp.351–357,1968). The media were harvested after 48 h transfection and then concentrated 10 times on Centricon 30 filters (Amicon) for the enzyme assay. For metabolic labeling, COS cells (60-mm culture dish) were washed with Met-free medium (Dulbecco's modified Eagle's medium and 2% fetal calf serum) (GIBCO) and then incubated for 1 h with the same media. The cells were pulse-labeled with 10 MBq/dish of Express $^{35}$S protein labeling mix (Du Pont-New England Nuclear) in 1.5 ml of Met-free media for 2 h. These cells were then washed with Met-free media and chased for 5 h in media without Express-label. The media containing secreted proteins were harvested, concentrated 10 times, and then subjected to SDS-PAGE, followed by fluorography.

The enzyme activity of the expressed protein was measured as follows. The assays using oligosaccharides and glycoproteins as acceptors were performed in the presence of 50 mM sodium cacodylate buffer (pH 6.0), 50 μM CMP-[$^{14}$C-]NeuAc (0.9 Bq/pmol), 1 mg/ml of bovine serum albumin, 2 mg/ml of acceptor substrate and 1 μl of concentrated COS cell medium, in a final volume of 10 μl and were incubated at 30° C. for 2 h. At the end of the incubation period, 1 μl of the assay mixture was applied to a Silica gel 60HPTLC plate (Merck, Germany). The plate was developed with ethanol:pyridine: n-butanol:water:acetate (100:10:10:30:3), and the radioactivity was visualized and quantified with a BAS2000 radio image analyzer (Fuji Photo Film, Japan). The radioactivity remaining at the origin was taken as sialylated glycoprotein.

Identification of the sialylated products was carried out as follows. Asialo-BSM were resialylated with CMP-[$^{14}$C] NeuAc in pcDSB-690 COS cell medium and β-elimination oligosaccharides were prepared. β-elimination was carried out according to Carlson's method (Carlson, D. M., J. Biol. Chem., 243, 616–626, 1968). Asialo-BSM (100 μg each) was sialylated with CMP-[$^{14}$C]NeuAc in pcDSB-690 COS cell medium under the same conditions as above, except that the incubation period was 12 h. The reaction was terminated by adding 500 μl of 1% phosphotungstic acid in 0.5M HCl, followed by centrifugation at 10,000×g for 5 min. The pellets were washed once with the same phosphotungstic acid solution and once with methanol, dissolved in 0.5 ml of 0.05M NaOH and 1M NaBH$_4$, and then incubated 30 h at 45° C.

At the end of the incubation period, the solution was neutralized with acetic acid to pH 6 and then lyophilized. The dehydrated products were dissolved in 50 μl of water, and then desalted by gel filtration on a Sephadex G-15 column (0.5×5 cm) equilibrated and eluted with water. The radioactive fractions were subjected to thin layer chromatography for identification of the products without further purification. NeuAc α 2,6GalNAc-ol and GlcNAc β 1,3 [NeuAc α 2,6]GalNAc-ol from native BSM in two different developing solvent were co-migrated. The ratio of the transferred sialyl residue was 1:0.9:0.6. The results of the co-migration of Sialylated GalNAc-SerNAc with with NeuAc α 2,6GalNAc-SerNAc in the two different solvent systems indicate that the protein SB-690 of the present invention forms the NeuAc α 2,6 linkage to GalNAc that is directly attached to Ser or Thr residues in glycoproteins.

Media from cells transfected with pcDSB-690 contained sialyltransferase activity and it provide strong evidence that the protein SB-690 of the present invention expressed by pcDSB-690 was secreted out of cells while retaining sialyltransferase activity. On the other hand, media obtained from cells transfected with cDSB-BGL had no sialyltransferase activity.

The acceptor specificity of the protein SB-690 of the present invention was examined with the concentrated COS-7 cell culture medium transfected with pcDSB-690. As shown in Table 1, asialo-mucin, fetuin and asialo-fetuin served as good acceptors. Remarkably, fetuin was shown to be a better acceptor than asialo-fetuin (Baubichon-Cortay, H. et al., Carbohydr. Res., 149, 209–223, 1986; and Brockhausen, I. et al., Biochemistry, 29, 10206–10212, 1990). Other glycoproteins, oligosaccharides and glycolipids did not serve as acceptors, except GalNAc-SerNAc. These data suggest that the acceptor site is GalNAc directly attached to Ser or Thr residues in glycoproteins through an α-glycoside linkage.

TABLE 1

Acceptor specificity of the protein SB-690 of the invention

| Acceptor | Pmoles/hr/10 μl medium |
|---|---|
| Fetuin | 142 |
| Asialo-fetuin | 96 |
| α 1 acid glycoprotein | 6 |
| Asialo- α 1 acid glycoprotein | 4 |
| Bovine submaxillary mucin | 15 |
| Bovine submaxillary asialo-mucin | 186 |
| Ovomucoid | 7 |
| Asialo-ovomucoid | 0 |
| Gal β 1,3GlcNAc β 1,3Gal β 1,4Glc | 0 |
| Gal β 1,4GlcNAc | 0 |
| Gal β 1,3GalNAc | 0 |
| GalNAc β 1,4 Gal | 0 |
| Gal β 1,4Glc | 0 |
| Galactose | 0 |
| Ganglioside mixture | 0 |
| Ganglioside GD1a | 0 |
| GalNAc-SerNAc | 4 |
| Benzyl-Ga1NAc | 2 |

*A number of 0 indicates less than 1 pmol/hr/10 μl medium.

so far cloned sialyltransferases only exhibit acceptor specificity for the Gal-moiety. While the GalNAc α 2,6-sialyltransferase P-B1 and protein SB-690 of the present invention exhibit acceptor specificity for the GalNAc- but not the Gal-moiety. The following evidence supports that GalNAc α 2,6-sialyltransferase P-B1 and the protein SB-690 of the present invention have the activity of GalNAc α 2,6-sialyltransferase, which transfer CMP-NeuAc with an α 2,6-linkage onto a GalNAc residue O-linked to Thr/Ser of a glycoprotein:
(i) The expression of pcDSB-690 in COS cells reveals the remarkable acceptor specificity for only the GalNAc moiety bound to Ser/Thr residues, while no detectable enzyme activity was found toward the other substrates tested (Table 1).
(ii) The sialylated products obtained from bovine submaxillary asialo-mucin and GalNAc-SerNAc were shown to have sialic acid bound to the GalNAc moiety through an α 2,6-linkage.

The two types, i.e., bovine submaxillary gland- and liver (brain)- types, of GalNAc-α 6ST were reported, which have the different acceptor specificity (Bergh, M. E. et al., J. Biol. Chem., 258, 7430–7436, 1983). The former enzyme has the broad specificity toward GalNAc, Gal β 1,3GalNAc and NeuAc α 2,3Gal β 1,3GalNAc, whereas the latter has only toward NeuAc α 2,3Gal β 1,3GalNAc moiety of glycoproteins. The acceptor specificities of the GalNAc α 2,6-sialyltransferase P-B1 and the protein SB-690 of the present invention were found to be similar to that of the former enzyme.

Examination of the acceptor site of asialo-mucin showed that NeuAc α 2,6GalNAc-Ser/Thr was the most abundant product. However, considering the ratio of glycoconjugates in bovine submaxillary asialo-mucin, i.e., GalNAc-Ser/Thr, GlcNAc β 1,3GalNAc-Ser/Thr, and Gal β 1,3GalNAc-Ser/Thr amounted to 65%, 25%, and 5%, respectively (Tsuji, T. and Osawa, T., Carbohydr. Res., 151, pp.391–402, 1986), GalNAc α 2,6-sialyltransferase P-B1 and the protein SB-690 of the present invention seem to have the following acceptor preference: Gal β 1,3GalNAc-Ser/Thr>GlcNAc β 1,3GalNAc-Ser/Thr>GalNAc-Ser/Thr. On the other hand, the facts that almost all radioactivity was released on weak alkali treatment and that fetuin is preferred over asialo-fetuin (Table 1) indicate that NeuAc α 2,3Gal β 1,3GalNAc-Ser/Thr is a preferred substrate over Gal β 1,3GalNA α-Ser/Thr, as reported for calf liver (Bergh, M. E. et al., J. Biol. Chem., 258, 7430–7436, 1983) and rat brain (Baubichon-Cortay, H. et al., Carbohydr. Res., 149, 209–223, 1986) GalNAc α 2,6-sialyltransferases.

The sialylation of GalNAc-SerNAc was much slower than that of corresponding residues on asialo-mucin (Table 1). Brockhausen et al. (Brockhausen et al., Biochemistry, 29, 10206–10212, 1990) showed that a length of at least five amino acid is required for efficient synthetase activity. A similar effect of the peptide portion directly on GalNAc α 2,6-sialyltransferase P-B1 and the protein SB-690 of the present invention is also suggested from this observation (Table 1).

The regents and the like used in the above preparation examples (A) and (B) were as follows: Fetuin, asialo-fetuin, bovine submaxillary mucin, α 1-acid glycoprotein, galactose β 1,4-N-acetylgalactosamine, CMP-NeuAc, lacto-N-tetraose, benzyl-GalNAc, N-acetyllactosamine, and Triton CF-54 were obtained from Sigma (St. Louis, USA). CMP [$^{14}$C]NeuAc(11 GBq/mmole) was obtained from Amersham (U.K.). N-Acetylgalactosamine β 1,4-galactose was a gift from Dr. Kajimoto (The institute of Physical and Chemical Research, RIKEN, Wako-shi, Saitama-ken, Japan). 2-Acetamide and 2-deoxy-galactosyl-α N-acetylserine (GalNAc-SerNAc) were synthesized according to Grundler and Schmidt (Grundler G., and Schmidt R. R., Liebigs Ann. Chem., 1984, 1826–1847, 1984). NeuAc α 2,6-GalNAc-SerNAc was prepared from NeuAc α 2,6GalNAc-Ser (MECT) by acetylation with anhydroacetate in pyridine-water. NeuAc α 2,6GalNAc-ol and GlcNAc β 1,3[NeuAc α 2,6]GalNAc-ol were prepared from bovine submaxillary mucin according to Tsuji and Osawa (Tsuji, T. and Osawa T., Carbohydr. Res., 151, 391–402, 1986) and identified by 270 MHz $^1$H and $^{13}$C NMR (Savage, A. V. et al., Eur. J. Biochem., 192, pp. 427–432, 1990; and Savage, A. V. et al., Eur. J. Biochem., 193, 837–843, 1990). Synthetic primers were synthesized with the Applied Biosystem 394 DNA synthesizer. Restriction endonucleases SmaI, EcoRI, BamHI, HindIII, SacI, XhoI, BglII and PstI were from Takara (Japan).

(C) Preparation of GalNAc α 2,6-sialyltransferase P-B3

In order to obtain CDNA clones of GalNAc α 2,6-sialyltransferases, PCR with two degenerate oligonucleotides (ST-107 and ST-205) was performed with chick embryo cDNA as a template. The fragment of the desired size of approximately 150 bp was purified by agarose gel electrophoresis. As a result of sequencing of the PCR products, it was revealed that they included those encoding Gal β 1,4GlcNAc α 2,6-sialyltransferase (Kurosawa, N., et al., Eur. J. Biochem., 219, 375–381, 1994) and GalNAc α 2,6-sialyltransferase P-B1, as well as a PCR product encoding a novel amino acid sequence, pCRB3. The identity of the sialylmotif of pCRB3 with those of above-mentioned sialyltransferases was 65 through 57%.

In order to identify the complete coding sequence of the gene, a young chicken testis cDNA library was screened with the cDNA insert of pCRB3. The screening about 5×10$^5$ independent clones yielded one positive clone, λ CEB3-T20, which has an insert size of 2.05 kb.

The nucleotide sequence of the cDNA clone included an open reading flame of 1212 bp, coding for 404 amino acids with a molecular mass of 45.8 kDa. The open reading frame starts with a methionine codon at nucleotide 1, with a conventional translation initiation sequence (Kozak, M. Nature, 308, 241–246, 1984), and ends with a TGA stop codon at nucleotide 1213. The open reading flame is flanked by a 5'-untranslated sequence of 384 bp and a 3'-untranslated sequence of 451 bp. The DNA sequence 5' of the initiation site contains stop codons in all three reading frames. The nucleotide sequence and deduced amino acid sequences of λ CEB3-T20 are shown in the SEQ ID No.3 of the sequence listings. The GalNAc α 2,6-sialyltransferase having this amino acid sequence was designated as P-B3.

This GalNAc α 2,6-sialyltransferase P-B3 (when the GalNAc α 2,6-sialyltransferase P-B1 is referred to as ST6GalNAcA, this enzyme is occasionally referred to as ST6GalNAcB) has type II transmembrane domain, containing a 17-amino acid N-terminal hydrophobic sequence bordered by charged residues, as has been found for all sialyltransferases cloned to date. Comparison of the primary sequence of GalNAc α 2,6-sialyltransferase P-B3 with other amino acid sequences in DNA and protein data banks revealed similarities in two regions to all of the cloned sialyltransferases.

One region (sialylmotif L) in the center of the GalNAc α 2,6-sialyltransferase P-B3, consisting of a 45 amino acid stretch, shows 64–24% sequence identity, whereas the other, in the COOH-terminal portion (sialylmotif S, residues 333–355), exhibits 78–43% identity. The overall amino acid sequence identity of GalNAc α 2,6-sialyltransferase P-B3 is 10% to chick Gal β 1,4GlcNA α 2,6-sialyltransferase (Kurosawa, N., et al., Eur. J. Biochem., 219, 375–381, 1994), 13% to chick Gal β 1,3GalNAc α 2,3-sialyltransferase (Kurosawa N. et al., Biochem. Biophys. Acta., 1244, 216–222, 1995), and 32% to chick ST6GalNAcA (22), respectively. These results suggest that the cloned gene belongs to the sialyltransferase gene family.

Details of the experiments are as follows.

Polymerase chain reaction (PCR)

PCR was performed using degenerate primers [5' primer ST107: TGGGCCTTGGII(A/C)AGGTGTGCTGTTG, and 3' primer ST-205: AGGCGAATGGTAGTTTTTG(A/T)GCCCACATC] deduced from conserved regions in Gal β 4GlcNAc-α 6STRL (Weinstein, J. et al., J. Biol. Chem., 262, 17735–17743, 1987), Gal β 4GlcNAc-α 6STHP (Grundmann, U. et al., Nucleic acids Res., 18, 667, 1990), and Gal β 3GalNAc-α 3STPS (Gillespie, W. et al., J. Biol. Chem., 267, 21004–21010, 1992). To obtain cDNA, poly (A)-rich RNA (2 μg) from 3 day-old chick embryos was incubated with an oligo-dT primer (Pharmacia), 1 mM each of dATP, dCTP, dGTP and dTTP, and 2 U/μl of RNase inhibitor (Promega) in 10 mM Tris-HCl (pH 8.3), 50 mM KCl, 1.5 mM MgCl$_2$ and 0.001% gelatin in 50 μl for 10 min at 0° C., and then for additional 60 min at 42° C. after the addition of 100 μU Moloney murine leukemia virus reverse transcriptase (BRL).

After heating at 94 ° C. for 3 min, cDNA prepared from 0.2 μg of poly(A)-rich RNA was used for the PCR experiment in a mixture comprising 10 mM Tris-HCl (pH 8.3), 50 mM KCl 1.25 mM MgCl$_2$ 0.001% gelatin, 200 μM of each dATP, dCTP, dGTP and dTTP, 2 U of Taq DNA polymerase (Promega), and 40 pmoles of each PCR primer in 50 μl. PCR amplification, 35 cycles, was carried out, each cycle consisting of denaturation at 96° C. for 45 sec, annealing at 50° C. for 60 sec, and extension at 72° C. for 60 sec. The PCR products were developed on a 3% agarose gel. The DNA/fragment corresponding to 150 bp was eluted from the gel (Qiaex kit; Qiagen), blunt-ended, kinated, and then subcloned into the SmaI site of pUC119, and finally sequenced.

Construction of a cDNA library

Total RNA was prepared from chick embryos (6 day-old) by the guanidinium thiocyanate method, followed by centrifugation in a 5.7M CsCl solution (Sambrook, J., Molecular Cloning: a Laboratory Manual, 2nd edition). Poly(A)rich RNA was purified with Oligotex-dT30 (Takara), and then employed for the construction of a cDNA library using λ ZAPII (Stratagene) and CDNA synthesis kits (Pharmacia) with an oligo-dT primer and random primers.

Screening of the CDNA library

The amplified cDNA library ($1 \times 10^6$ plaques) was screened with the chick embryo PCR fragments. The plaque-transferred filters were hybridized with $^{32}$P-radiolabeled DNA probes for 12 h at 65° C. in 5× SSC, 0.2% SDS, 5× Denhardt's solution, and 10 μg/ml denatured salmon sperm DNA. The filters were then washed twice at 65° C. for 20 min in 2× SSC, 0.1% SDS. To obtain plasmids from the isolated phage clones, phagemid rescue was performed according to the instructions of the manufacturer of the λ ZAPII cloning kit (Stratagene). cDNA inserts were excised directly as Bluescript plasmids. Plasmids were produced by the standard molecular cloning method according to Sambrook, et al. (Sambrook, J. et al., Molecular Cloning: a Laboratory Manual, 2nd ed.).

DNA sequence analysis

The DNA sequences of the inserts were determined by the dideoxy-chain termination method (Sanger, F. et al., Proc. Natl. Acad. Sci. USA, 74, 5463–5467, 1977) using single-strand DNA as a template for T7-DNA polymerase. The sequencing reaction and electrophoresis were carried out using an AutoRead DNA sequencing kit and a DNA sequencer (Pharmacia). Single Strand DNA was prepared from *Escherichia coli* XL-Blue (Stratagene) after superinfection with helper phage R408 (Stratagene). The sequence data were analyzed with a computer using PC/Gene (Teijin System Technology).

To confirm the existence of the gene, Southern blot analysis was performed for chicken genomic DNA. Hybridization of the cDNA insert of pCRB3 for chicken genomic DNA gave a single band on digestion with EcoRI and two bands with BamHI. This simple hybridization pattern indicates that the cloned cDNA was a single copy gene. Southern blot analysis of genomic DNA from mouse and monkey with the pCRB3 probe under low stringency conditions suggested that this gene is conserved across species. For Southern blot, each 7.5 μg of genomic DNA prepared from mouse brain, COS-7 cells and chicken testes were digested with restriction enzyme and then size-fractioned on 0.6% agarose gels.

The mRNA size and distribution of the GalNAc α 2,6-sialyltransferase P-B3 gene were determined by Northern blot analysis. Analysis of RNA from 3, 6, 8, 10 and 12-day old embryos revealed two RNA species of 4.5 kb and 2.2 kb. The 4.5 kb mRNA was expressed abundantly at all embryonic stages examined, while not expressed in adult tissues. The less abundant 2.2 kb mRNA was expressed at the early embryonic stage, being abundant at the late embryonic stage and in adult tissues. The size of the 2.2-kb transcript suggests that the obtained cDNA clone (λ CEB3-T20) was close to full length. For Northern blots, 5 μg of poly(A)-rich RNAs from chick embryo and 10 μg of all RNA from chicken tissues were size-fractioned on formaldehyde-agarose gels.

Sialyltransferases previously known exhibit remarkable tissue-specific expression, which is considered to be correlated with the existence of cell type-specific carbohydrate structures (Paulson, J. C. and Colley, K. J., J. Biol. Chem., 264, pp.17615–17618, 1989). The results of Northern blotting indicate that the pattern of expression of sialyltransferase P-B3 changes. The precise structure of embryo-specific 4.5 kb mRNA has not been known. However, the production of two different sizes of mRNAs from the sialyltransferas e P-B3 gene suggests that they are very likely to be generated through alternative splicing and alternative promoter utilization mechanisms as observed for Gal β 1,4GlcNAc-α 2,6-sialyltransferase (Gal β 4GlcNAc-α 6STRL) and Gal β 1,3(4)GlcNAc α 2,3-sialyltransferase (Gal β 3(4)GlcNAc-α 3STRL) (Weinstein, J. et al., J. Biol. Chem., 262, 17735–17743, 1987; and Wen, D. X. et al., J. Biol. Chem., 267, 21011–21019, 1992). This hypothesis is supported by the results of Southern hybridization, which showed the existence of a single copy gene for sialyltransferase P-B3.

A 1.3 kb DNA fragment encoding the full length sialyltransferase P-B3 was amplified using synthetic oligonucleotide primers (5'-ACGGCGCTCGAGCCAACCCGGAGAGCAGCG-3', and 5'-CGTTGC CTCGAGAGTCCTTGCAGTGGGACT-3', synthetic XhoI site underlined). The amplified DNA fragment was digested with XhoI and inserted into the XhoI site of the expression vector pcDSR α (Takebe, Y., Mol. Cell. Biol., 8, pp.466–472, 1988) to yield recombinant plasmid pcDB3ST. The insert of the plasmid was sequenced to confirm the absence of possible polymerase chain reaction errors.

COS-7 cells were transfected with 5 μg of the recombinant plasmid pcDB3ST using the DEAE-dextran method (McCutchan, J. H. and Pagano, J. S., J. Natl, Cancer Inst., 41, 351–357, 1968).

After 48 h of the transfection, the cultured cells ($1 \times 10^7$) were harvested, washed with phosphate-buffered saline, and then resuspended in 2 ml of buffer comprising 20 mM $MnCl_2$ and 25 mM MES, pH 6.0. The cell suspension was centrifuged at 30,000×g for 30 min, the cell pellet was resuspended in 0.5 ml or 1% Triton X-100, 50 mM NaCl, 5 mM $MnCl_2$, 25 mM MES, pH 6.0, and then subjected to sonication. After centrifugation at 30,000×g for 30 min, the supernatant was concentrated 10-fold on Centricon 30 filters (Amicon), and then used for following assays.

The enzyme assays with glycoproteins, oligosaccharides and glycolipids as acceptors were performed in the presence of 0.1M sodium cacodylate buffer (pH 6.0), 10 mM $MgCl_2$, 0.5% Triton CF54, 12 μM CMP-[$^{14}$C]NeuAc (1.5 kBq), 1 mg/ml acceptor substrate, and 1 μl of COS cell lysate (in a final volume of 10 μl), with incubation at 37° C. for 1 hr. At the end of the incubation period, the reaction mixtures were subjected to SDS-PAGE for glycoproteins as acceptors, or were subjected to chromatography on HPTLC plates (Merck, Darmstadt, Germany) with a solvent system of ethanol/1-butanol/pyridine/acetic acid/water (100:10:10:3:30) for oligosaccharides and glycolipids as acceptors. Sialylated acceptors were quantified with a BAS2000 radio image analyzer (Fuji Photo Film, Japan).

Identifications of sialylated products were as follows. Reduced oligosaccharides were obtained from resialylated glycoproteins by β-elimination as described by Carlson (Carlson, D. M., J. Biol. Chem., 243, pp616–626, 1968). AsialoBSM was sialylated with CMP-[$^{14}$C]NeuAc in a pcDB3ST-transfected COS-7 cell lysate under the same conditions as above. The radiolabeled oligosaccharides released from fetuin were digested with NDV sialidase, and then subjected to thin layer chromatography for identification of the products without further purification. Oligosaccharides released from BSM were used as standards. AsialoBSM and asialofetuin were [$^{14}$C]-sialylated with the GalNAc α 2,6-sialyltransferase P-B1 and Gal β 1,3GalNAc α 2,3-sialyltransferase (Lee, Y.-C., et al., Eur. J. Biochem., 216, pp. 377–385, 1993), respectively, and the oligosaccharides were prepared by β-elimination. The resulting [$^{14}$C] NeuAc α 2,6GalNAc-ol, Gal β 1,3([$^{14}$C]NeuAc α 2,6) GalNAc-ol and [$^{14}$C]NeuAc α 2,3Gal β 1,3GalNAc-ol were used as radio-labeled standards.

When fetuin was used as the acceptor, the acceptor was only sialylated by the lysate of COS-7 cells transfected with pcDB3ST. The expressed GalNAc α 2,6-sialyltransferase P-B3 exhibited strong activity toward fetuin and asialofetuin, and weak activity toward asialoBSM, whereas no significant activity was observed toward BSM or other glycoproteins having only N-glycosidically linked oligosaccharides (e.g., α 1-acid glycoprotein, ovomucoid, asialo-α 1 acid glycoprotein and asialo-ovomucoid) (Table 2).

In addition, oligosaccharides or glycosphingolipids could not serve as acceptors for the GalNAc α 2,6-sialyltransferase P-B3 of the present invention. [$^{14}$C]NeuAc residues incorporated into fetuin by the enzyme were resistant to treatment with N-glycanase or NDV sialidase. The radiolabelled oligosaccharides released from fetuin were co-migrated with Gal β 1,3(NeuAc α 2,6)GalNAc-ol after treatment with NDV sialidase. These results indicate that sialic acid residues were transferred through α 2,6-linkages on GalNAc residues of O-glycosidically linked oligosaccharides of fetuin. Thus, the expressed enzyme apparently has GalNAc α 2,6-sialyltransferase activity. However, asialoBSM was a much poorer acceptor than fetuin and asialofetuin for this GalNAc α 2,6-sialyltransferase P-B3 of the present invention. The acceptor substrate specificity is different from that of the GalNAc α 2,6-sialyltransferase P-B1 for which asialoBSM serves as a much better acceptor than asialofetuin.

To define the substrate specificity of the GalNAc α 2,6-sialyltransferase P-B3 of the present invention, fetuin was sequentially treated with sialidase (*Vibrio cholerae*) and β-galactosidase (bovine testes), and the resulting asialofetuin and agalacto-asialofetuin were used as acceptors. The incorporation of NeuAc-residues for the sialidase-treated fetuin was increased 1.5-fold of that for native fetuin. Three O-glycosidically linked oligosaccharides are known to be contained in fetuin, two of which are NeuAc α 2,3 Gal β 1,3GalNAc and the other is NeuAc α 2,3Gal β 1,3(NeuAc α 2,6)-GalNAc (Spiro, R. G. and Bhoyroo, V. D., J. Biol. Chem., 249, 5704–5717, 1974). Accordingly, GalNAc residues in two of the three O-linked oligosaccharides can serve as acceptors in native fetuin, whereas those in all O-linked oligosaccharides in asialofetuin can be sialylated by the GalNAc α 2,6-sialyltransferase P-B3 of the present invention.

Furthermore, agalacto-asialofetuin could not serve as an acceptor of the GalNAc α 2,6-sialyltransferase P-B3 of the present invention, and only Gal β 1,3([$^{14}$C]NeuAc α 2,6) GalNAc-ol, but not [$^{14}$C]NeuAc α 2,6-GalNAc-ol, was detected for the oligosaccharides released from asialoBSM incubated with the enzyme by β-elimination.

The characteristics of the GalNAc α 2,6-sialyltransferase P-B3 of the present invention revealed by the above experiments can be summarized as follows:

(1-i) Fetuin and asialofetuin, which contain the O-glycosidically linked (NeuAc α 2,3)Gal β 1,3GalNAc sequence (Spiro, R. G. and Bhoyroo, V. D., J. Bio. Chem., 249, 5704–5717, 1974), served as good acceptors, but asialoBSM, in which only 5% of the total carbohydrate chains contain Gal β 1,3GalNAc sequences (Tsuji, T. and Osawa, T., Carbohydr. Res., 151, 391–402, 1986), served as a much poorer acceptor; and (1-ii) the protein portion is essential for the activity of this sialyltransferase, since Gal β 1,3GalNAc α 1-Bz as well as asialoGM1 (Gal β 1,3GalNAc β 1,4Gal β 1,3Glc β 1-Cer) and GM1b (NeuAc α 2,3Gal β 1,3GalNAc β 1,4Gal β 1,3Glc β 1-Cer) did not serve as acceptors.

(2) This sialyltransferase did not exhibit activity toward asialofetuin treated with β-galactosidase (agalacto-asialofetuin).

(3) Only Gal β 1,3([$^{14}$C]NeuAc-α 2,6)GalNAc-ol was detected in the oligosaccharides released from [$^{14}$C] sialylated asialoBSM although about 60% of the carbohydrate chains of asialoBSM are GalNAc-O-Ser/Thr (Tsuji, T. and Osawa, T., Carbohydr. Res., 151, 391–402, 1986).

These results clearly suggest that the acceptor substrate of the enzyme of the present invention having catalytic activity, i.e., transfer of CMP-NeuAc with an α 2,6-linkage onto a GalNAc residue O-linked to Thr/Ser of a glycoprotein, requires Gal β 1,3 GalNAc sequence of O-glycoside linked oligosaccharide, whereas α 2,3 linkage-sialic acid residues linked to galactose residues are not essential for the activity. Therefore, the enzyme P-B3 first cloned by the present invention is a novel type of GalNAc α 2,6-sialyltransferase. The primary sequence of GalNAc α 2,6-sialyltransferase P-B3 from the 45 amino acid regions at the molecular center (sialylmotif L) to the COOH-terminal (residues: 180–404) exhibits high sequence homology to that of GalNAc α 2,6-sialyltransferase P-B1 (FIG. 4: the identity is 48%). The conserved regions unique to these GalNAc α 2,6-sialyltransferases may be correlated with their enzymatic function of transferring sialic acid to the GalNAc-moiety via an α 2,6-linkage.

TABLE 2

Acceptor substrate specificity of GalNAc α 2,6-sialyltransferase P-B3 of the invention

| Acceptor | Specificity pmol/h/µl enzyme fraction |
|---|---|
| Fetuin | 28 |
| Asialofetuin | 35 |
| BSM | 0.5 |
| AsialoBSM | 5.2 |
| α 1-Acid glycoprotein | 0 |
| Asialo- α 1-acid glycoprotein | 1.2 |
| Ovomucoid | 0 |
| Asialo-ovomucoid | 1.0 |
| Gal β 1,3GalNAc α 1-Bz | 0 |
| GalNAc α 1-Bz | 0 |
| GalNAc-SerNAc | 0 |
| AsialoGM1 | 0 |
| GM1b | 0 |
| Ganglioside Mixture | 0 |

0 indicates less than 0.5 pmol/h.

The regents, samples and the like used in the above preparation example (C) were as follows. Fetuin, asialofetuin, bovine submaxillary mucin, α 1-acid glycoprotein, galactose β 1,4-N-acetylgalactosamine, CMP-NeuAc, Gal β 1,3GalNAc α 1-Bz, GalNAc α 1-Bz and Triton CF-54 were obtained from Sigma (St. Louis, USA). CMP-[$^{14}$C]NeuAc (11 GBq/mmole) was obtained from Amersham (U.K.). 2-Acetamide and 2-deoxygalactosyl α N-acetylserine (GalNAc-SerNAc) was synthesized according to Grundler and Schmidt (Grundler G., and Schmidt R. R., Liebigs Ann. Chem., 1984, 1826–1847, 1984). NDV-sialidase and sialidase from *Vibrio cholerae* were purchased from Oxford Glycosystems (U.K.) and Boehringer Mannheim (Germany), respectively. p-Galactosidase from bovine testes was obtained from Boehringer Mannheim (Germany). Synthetic primers were synthesized with the Applied Biosystem 394 DNA synthesizer. Restriction endonucleases were obtained from Takara (Japan)

(D) Purification of sialyltransferase expressed in microorganisms

Plasmid construction

An initiation codon and cloning sites were attached by PCR to mouse Gal β 1,4GlcNAc α 2,6-Sialyltransferase cDNA (Hamamoto, T. et al., Bioorg. Medicin. Chem., 1, 141–145, 1993). 5'-TGGCATATGGGGAGCG ACTATGAGGCTCT-3' containing an NdeI site was used as a sense primer and 5'-ATGAGGATCCCTGGCTCAACAGCG-3' containing a BamHI site as an antisense primer. The resulting PCR fragment (1152 bp) contained the initiation codon and a region coding for a polypeptide from the 29th amino acid residue to the C-terminal end of the enzyme, and lacked the cytosolic and transmembrane domains. The fragment was incorporated into expression vector pET3b (Studier, F. W. et al., Method. Enzymol., 185, 60–89, 1990) at the NdeI-BamHI site (located downstream of the T7 promoter). The resulting recombinant vector was named as pET3-MBS. The nucleotide sequence of the PCR fragment is shown as the SEQ ID No.4 in the sequence listings.

Enzyme expression

E. coli JM109(DE3) cells transfected with the vector pET3-MBS were cultured in 100 ml LB medium supplemented with 100 µg/ml ampicillin at 37° C. When the optical density at 600 nm reached 0.2–0.4, production of the recombinant protein was initiated with induction of T7 RNA polymerase by the addition of 2 mM IPTG (isopropyl β-D-thiogalatopyranoside). The recombinant enzyme, lacking the cytosolic and the transmembrane domain, was accumulated in the form of insoluble inclusion bodies in the cells. The growth rate of the JM109(DE3) cells transfected with pET3-MBS was the same as that of the non-transfected JM109(DE3) cells both on agar plates and in liquid culture. After 2 h cultivation, the cells were harvested (ca. 1 g wet weight), suspended in 10 ml of 20 mM Tris-HCl (pH 8.0), and then treated with lysozyme (0.1 mg/ml) and DNase I (0.01 mg/ml) for 30 min. Triton X-100 was added to a final concentration of 1%, and insoluble fraction was collected by centrifugation at 12,000×g for 15 min at 4° C. The precipitate was suspended in 3 ml of 10 mM Tris-HCl (pH 7.4) and stored at −30° C. before use.

Solubilization and renaturation

To 0.5 ml of the above suspension, 0.48 g solid urea, 60 µl of 5M NaCl, 20 µl of 1M Tris-HCl (pH 7.4) and water were added to final volume of 1 ml (final concentration: 8M urea, 0.3M NaCl; 20 mM Tris-HCl, pH 7.4). The precipitate was extracted for 30 min at 10° C., followed by centrifugation at 12,000×g for 15 min. Most of the extracted protein had the molecular mass of 42 k dalton. Where 5.7M urea buffer was used for the extraction, 80% of the enzyme was recovered.

The 0.1 ml aliquots of extract containing 8M urea were diluted with each 1.9 ml of a renaturation composition (standard composition: 2M urea, 0.5M NaCl, 10 mM lactose, 0.5 mM EDTA, and 20 mM MOPS-NaOH, pH 7.0) to a final protein concentration of about 0.02 mg/ml. The solution was left at 40° C. for 12 h, and then diluted again with an equal volume of the renaturation composition, thereby reducing the urea concentration to half (approximately 1.2M), and then the mixture was left at 40° C. for additional 48 h. Then, sialyltransferase activity was measured to analyze the effects of the components of the renaturation composition at this point (Table 3). The resulting enzymes were further dialyzed against the renaturation composition to remove residual urea and the reducing agents over 48 h at 4° C. The samples were concentrated approximately 20 times with Centricon-30 (Amicon).

Sialyltransferase assay

The activity of the sialyltransferase was measured with 50 µM CMP-[$^{14}$C]NeuAc (0.9 Bq/pmole) as a donor substrate, and 5 mM Gal β 1,4GlcNAc (N-acetyllactosamine) as an acceptor substrate. Reaction mixture was added with 1 mg/ml bovine serum albumin, 1 µl of the enzyme solution, and 50 mM sodium cacodylate (pH 6.0) to a total volume of 10 µl, and incubation was continued at 37° C. for 1 h. Then, the samples were applied to silica gel60 HPTLC plate (Merck Germany) and developed with ethanol/pyridine/n-butanol/acetic acid/water (100:10:10:3:30) as a developing solvent. The radioactivity transferred on each plate was determined with a radio image analyzer BAS2000 (Fuji Photo Film, Japan, Lee, Y.-C. et al., Eur. J. Biochem., 216, 377–385, 1993). One unit of enzymatic activity was defined as an amount catalyzing 1µ mole of sialic acid transfer per minute. The acceptor preference as to oligosaccharide branches was examined using a N-acetyllactosamine type biantennary pyridylamino-oligosaccharide as an acceptor substrate and analyzed fluorophotometrically by HPLC.

When the 8M urea extract was dialyzed without dilution at 4° C., almost no activity of the enzyme precipitated at urea concentration of less than 0.5M was recovered. The results of the optimum dilution conditions at 48 h after the second dilution are shown in Table 3 set out below. In the table, the standard renaturation composition was comprised of: 2M urea, 20 mM Tris-HCl, 0.3M NaCl, 20 mM lactose, and 0.5 mM EDTA (pH 7.4), and as to other compositions, deviations from the standard composition are indicated.

TABLE 3

The effects of various conditions on renaturation of Gal β 1,4GalNAc α 2,6-sialyltransferase

| Renaturation conditions | Relative activity compared to standard |
| --- | --- |
| Standard composition | 1 |
| pH 9.5, Tris-HCl 20 mM | 0* |
| pH 8.0, Tris-HCl 20 mM | 0.6 |
| pH 7.0, MOPS-NaOH 20 mM | 2.5 |
| pH 6.0, MES-NaOH 20 mM | 1.5 |
| 0.5 M NaCl | 2 |
| 0.1 M NaCl | 0.2 |
| 0.01 M NaCl | 0 |
| 0 mM lactose | 0.5 |
| 1 M urea | 1.5 |
| 0 M urea | 0.6 |

*A value of 0 indicates less than 5% of the control.

The maximum renaturation was observed with 0.5M NaCl (pH 7.0) in the standard composition, and these compositions were used in further experiments. After three independent renaturation experiments were carried out under this condition, total recovered activities were 0.4–0.8 mU/0.1 ml extract. The enzymes at this stage of renaturation showed high Km values for CMP-NeuAc and N acetyllactosamine, 0.14 mM and 20 mM, respectively. Under the conditions tested, reducing agents (DTT and β-mercaptoethanol) inhibited the enzyme activity, which may be due to the carryover of urea at the concentration of 0.1M in the assay mixture. In addition, very little activity was observed at 12 h after the second dilution, which apparently indicates that a refolding process of the polypeptide is very slow at the test temperature. Almost the same activity, as that in the process without the use of the reducing reagents, was obtained by the following process: the 8M urea extract was diluted with 20 volumes of the renaturation composition containing 2M urea, 20 mM MOPS-NaOH, pH 7.0, 0.5M NaCl, 20 mM lactose, and 0.5 mM EDTA in the presence of 1M or 1 mM reducing regents, and then samples were left at 4° C. for 12 h and diluted to reduce the urea concentration to half, and the residual urea and reducing reagents were removed by dialysis. The results are shown in Table 4.

TABLE 4

| Reducing regent | Specific activity (mU/mg) |
|---|---|
| None | 7 |
| 1 μM DTT | 6 |
| 1 mM DTT | 12 |

The substrate specificity of renatured mouse Gal β 1,4GlcNAc α 2,6-sialyltransferase was assayed using each 2 mg/ml of substrates. The products were analyzed by HPTLC. HPTLC was performed using ethanol/pyridine/n-butanol/acetic acid/water (100:10:10:3:30) as a developing solvent when oligosaccharides and glycoproteins were used as acceptors, and chloroform:methanol:0.5% $CaCl_2$ (55:45:8) as a developing solvent when glycolipids were used as acceptors. The substrate specificity and kinetic parameters of the renatured enzymes were similar to those of the enzyme obtained from rat liver. The results are shown in Table 5 and Table 6.

TABLE 5

| | Relative Activity to Gal β 1,4GlcNAc | |
|---|---|---|
| Substrate | Renatured mouse Gal β 1,4GlcNAc α 2,6-sialyltransferase | Rat liver Gal β 1,4GlcNAc α a2,6-sialyltransferase |
| Fetuin | 0.25 | 0* |
| Asialofetuin | 1.5 | 0.97 |
| α 1 acid glycoprotein | 0.1 | 0.1 |
| Asialo-α 1 acid glycoprotein | 2.1 | 1 |
| Bovine submaxillary mucin | 0 | 0 |
| Bovine submaxillary asialo-mucin | 0 | 0 |
| Lacto N-tetraose | 0 | 0 |
| Gal β 1,4GlcNAc | 1 | 1 |
| Gal β 1,3GlcNAc | 0 | 0 |
| GalNAc β 1,4Gal | 0 | 0 |
| Gal β 1,4Glc | 0 | 0 |
| Gal | 0 | 0 |

*A value of 0 indicates less than 2% of the control.

TABLE 6

| | Km (mM) | |
|---|---|---|
| Substrate | Renatured mouse Gal β 1,4GlcNAc α 2,6-sialyltransferase | Rat liver Gal β 1,4GlcNAc α a2,6-sialyltransferase |
| CMP-NeuAc* | 0.08 | 0.04 |
| N-acetyllactosamine | 6.5 | 5 |
| Asialo-orosomucoid** | 0.4 | 0.2 |

*Measured with N-acetyllactosamine as the acceptor.
**Concentration expressed as terminal galactose residues.

Gal β 1,4GlcNAc α 2,6-sialyltransferase is capable of recognizing the different branches of biantennary glycopeptides of the N-acetyllactosamine type (Joziasse, D. H. et al., J. Biol. Chem., 260, 714–719, 1985; and Van den Eijnden D. H. et al., Biochem. Biophys. Res. Comm., 92, 839–845, 1980). A desialylated biantennary PA-oligosaccharide was sialylated by the enzyme renatured according to the method of the present invention and then analyzed with HPLC. The assays were performed using 10 pmoles of acceptor substrates and 0.1 mM CMP-NeuAc in a final volume of 5 μl. The reaction mixtures were incubated at 37° C. for 1 h, and the reaction was stopped by the addition of 90 μl of cold water. To identify sialylated pyridylamino oligosaccharides, each reaction mixture was subjected to HPLC analyses equipped with a reversedphase column (Shimpack CLC-ODS, 0.6 cm×15 cm, Shimazu, Japan). The column was equilibrated with mixture of 70% solvent A (10 mM sodium phosphate, pH 3.8) and 30% solvent B (0.5% n-butanol, 10 mM sodium phosphate, pH 3.8), and eluted at the flow rate of 1 ml/min with a linear gradient of solvent B to 60% over 30 min at 55° C. Pyridylamino oligosaccharides were detected fluorophotometrically (excitation at 320 nm and emission at 400 nm), and the results indicated that the renatured enzyme showed higher preference for galactose residues on Man α 1,3 branches rather than for galactose residues on Man α 1,6 branches like the native enzyme.

By competely remove urea, the renatured enzyme restored its resistance to reducing agents. In addition, more than 10 times activation was recovered by renaturing with the addition of divalent cations. While not bound by any specific theory, where dialysis is carried out for a prolonged period of time against a dialysis buffer containing 0.5 mM EDTA in the presence of urea, divalent cations, which are tightly bound to the enzyme to maintain the proper conformation of the enzyme, may be lost. Where the enzyme was renatured in the renaturation composition containing 1.2M urea, the addition of divalent cations increased the activity. The results obtained are shown in Table 7. In the table, the activities are shown as relative values to that obtained by no addition of reagents. The specific activity of the renatured enzyme was 0.15 U/mg protein when measured with 5 mM $MnCl_2$, which is about 2% of that of the enzyme obtained from rat liver (Weinstein, J. et al., J. Biol. Chem., 257, pp.13835–13844, 1982). The overall recovery of the enzyme was 0.1 U/100 ml culture medium.

TABLE 7

| Reagent | Renatured mouse Gal β 1,4GlcNAc α 2,6-sialyltransferase | Rat liver Gal β 1,4GlcNAc α 2,6-sialyltransferase |
|---|---|---|
| Reducing agent | | |
| DTT (1 mM) | 1.0 | 0.9 |
| (1 μM) | 1.1 | 1.2 |
| Mercaptoethanol (1 mM) | 1.1 | 1.1 |
| (1 μM) | 1.0 | 1.1 |
| Detergent | | |
| Triton x-100 (1%) | 1.5 | 0.8 |
| (0.5%) | 1.4 | 1.4 |
| (0.1%) | 1.3 | 1.3 |
| Divalent cations | | |
| $MgCl_2$ (5 mM) | 11 | 1.0 |
| $MnCl_2$ (5 mM) | 13 | 1.1 |
| EDTA (5 mM) | 1.7 | 0.9 |

The method of the present invention was specifically explained above referring to the examples relating to the Gal β 1,4GlcNAc α 2,6-sialyltransferase. However, the method of the present invention is not limited to these examples. As described above, unlike other glycosyltransferases, sialyltransferases share highly conserved regions (sialylmotif, Livingston, B. D. and Paulson, J. C., J. Biol. Chem., 268, 11504–11507, 1993), and all of the sialyltransferases are considered to have similar higher-order structures (Drickamer, K., Glycobiology, 3, 2–3, 1993). Therefore, it is readily understood by those skilled in the art that the renaturation procedure disclosed in the above examples for Gal β 1,4GlcNAc α 2,6-sialyltransferase can be applied to renaturations of other sialyltransferases to achieve the same advantageous effects. Furthermore, those skilled in the art will be able to choose optimum renaturing conditions, not only for Gal β 1,4GlcNAc α 2,6-sialyltransferase but for other sialyltransferases, by modifying or altering the processes disclosed in the specification.

The regents and samples used in the above example (D) were as follows. Rat liver Gal β 1,4GlcNAc α 2,6-sialyltransferase, fetuin, asialo-fetuin, bovine submaxillary mucin, α 1-acid glycoprotein, galactose β 1,3-N-acetylgalactosamine, lacto N-tetraose and N-acetyllactosamine were obtained from Sigma (St. Louis, USA). Urea was purchased from Wako Pure Chemicals (Osaka, Japan) and a solution was prepared just before use. CMP-[$^{14}$C]NeuAc (11 GBq/mmole) was obtained from Amersham (U.K). Bovine submaxillary asialo-mucin and asialo-α 1-acid glycoprotein were obtained by mild acid treatment of corresponding glycoproteins. N-acetylgalactosamine β 1,4-galactose was a kind gift from Dr. Kajimoto (The institute of Physical and Chemical Research, RIKEN, Wako-shi, Saitama-ken, Japan). Pyridylamino oligosaccharides (PA-sugar 001, 021, 022 and 023) were obtained from Takara (Kyoto, Japan). Protein concentrations were determined with a BCA protein assay kit (Pierce) using bovine serum albumin as the standard. Dialysis tubing (20/32) was from Viskase.

Industrial applicability

The novel GalNAc α 2,6-sialyltransferases P-B1 and P-B3, and proteins which contain a polypeptide part as being the active domain of said enzymes and are released extracellularly provided by the present invention are useful as, for example, reagents for introducing human type sugar-chain to proteins and medicament for treating hereditary diseases lacking human-specific sugar chains. In addition, they can be used as drugs for inhibiting tumor metastases, preventing viral infection, and controlling inflammatory reaction. Furthermore, the method of the present invention is useful when a large quantity of a sialyltransferase is expressed in microorganisms, since it enables a mass recovery of the enzyme with highly restored activity from aggregate or precipitate inside the cells.

---

What is claimed is:

1. An extracellularly releasable recombinant fusion protein comprising the active domain of a GalNAc α 2,6-sialyltransferase and a signal peptide.

2. The protein according to claim 1, wherein the GalNAc α 2,6-sialyltransferase is GalNAc α 2,6-sialyltransferase P-B1 having the amino acid sequence set forth in SEQ ID NO.5.

3. The protein according to claim 1, wherein the GalNAc α 2,6-sialyltransferase is encoded by the nucleic acid sequence set forth in SEQ ID NO.1.

4. The protein according to claim 1, wherein the active domain comprises amino acid 233 to amino acid 566 set forth in SEQ ID NO.5.

5. The protein according to claim 1, wherein the active domain is encoded by the nucleic acid sequence from nucleotide 697 to nucleotide 1698 set forth in SEQ ID NO.1.

6. The protein according to claim 1, wherein the GalNAc α 2,6-sialyltransferase is GalNAc α 2,6-sialyltransferase P-B3 having the amino acid sequence set forth in SEQ ID NO.7.

7. The protein according to claim 1, wherein the GalNAc α 2,6-sialyltransferase is encoded by the nucleic acid sequence set forth in SEQ ID NO.3.

8. The protein according to claim 1, comprising the amino acid sequence set forth in SEQ ID NO.6.

9. The protein according to claim 1, which is encoded by the nucleic acid sequence set forth in SEQ ID NO.2.

10. An extracellularly releasable recombinant fusion protein, comprising the active domain of GalNAc α 2,6-sialyltransferase and a signal peptide, wherein said signal peptide is located on the N-terminal side of the active domain and replaces the hydrophobic segment of the GalNAc α 2,6-sialyltransferase.

11. The protein according to claim 10, wherein the GalNAc α 2,6-sialyltransferase is GalNAc α 2,6-sialyltransferase P-B1 having the amino acid sequence set forth in SEQ ID NO.5.

12. The protein according to claim 10, wherein the GalNAc α 2,6-sialyltransferase is encoded by the nucleic acid sequence set forth in SEQ ID NO.1.

13. The protein according to claim 10, wherein the active domain comprises amino acid 233 to amino acid 566 set forth in SEQ ID NO.5.

14. The protein according to claim 10, wherein the active domain is encoded by the nucleic acid sequence from nucleotide 697 to nucleotide 1698 set forth in SEQ ID NO.2.

15. The protein according to claim 10, wherein the GalNAc α 2,6-sialyltransferase is GalNAc α 2,6-sialyltransferase P-B3 having the amino acid sequence set forth in SEQ ID NO.7.

16. The protein according to claim 10, wherein the GalNAc α 2,6-sialyltransferase is encoded by the nucleic acid sequence set forth in SEQ ID NO.3.

17. The protein according to claim 10, comprising the amino acid sequence set forth in SEQ ID NO.6.

18. The protein according to claim 10, which is encoded by the nucleic acid sequence set forth in SEQ ID NO.2.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 2671
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:1:

```
ATG  GGG  TTT  TTA  ATC  AGA  AGG  CTT  CCT  AAA  GAT  TCC  AGA  ATA  TTC      45
MET  Gly  Phe  Leu  Ile  Arg  Arg  Leu  Pro  Lys  Asp  Ser  Arg  Ile  Phe
 1              5                        10                       15

CGT  TGG  CTC  CTT  ATT  TTA  ACA  GTC  TTT  TCC  TTC  ATC  ATT  ACT  AGT      90
Arg  Trp  Leu  Leu  Ile  Leu  Thr  Val  Phe  Ser  Phe  Ile  Ile  Thr  Ser
                 20                       25                       30

TTT  AGC  GCC  TTG  TTT  GGC  ATG  GAG  AAA  AGC  ATT  TTC  AGG  CAG  CTC     135
Phe  Ser  Ala  Leu  Phe  Gly  MET  Glu  Lys  Ser  Ile  Phe  Arg  Gln  Leu
            35                           40                   45

AAG  ATT  TAC  CAA  AGC  ATT  GCA  CAT  ATG  CTA  CAA  GTG  GAC  ACC  CAA     180
Lys  Ile  Tyr  Gln  Ser  Ile  Ala  His  MET  Leu  Gln  Val  Asp  Thr  Gln
         50                       55                       60

GAT  CAG  CAA  GGT  TCA  AAC  TAT  TCT  GCT  AAT  GGG  AGA  ATT  TCA  AAG     225
Asp  Gln  Gln  Gly  Ser  Asn  Tyr  Ser  Ala  Asn  Gly  Arg  Ile  Ser  Lys
 65                       70                       75

GTT  GGT  TTG  GAG  AGA  GAC  ATT  GCA  TGG  CTC  GAA  CTG  AAT  ACT  GCT     270
Val  Gly  Leu  Glu  Arg  Asp  Ile  Ala  Trp  Leu  Glu  Leu  Asn  Thr  Ala
                 80                       85                       90

GTG  AGT  ACA  CCA  AGT  GGG  GAA  GGG  AAG  GAA  GAG  CAG  AAG  AAA  ACA     315
Val  Ser  Thr  Pro  Ser  Gly  Glu  Gly  Lys  Glu  Glu  Gln  Lys  Lys  Thr
            95                          100                  105
```

```
GTG  AAA  CCA  GTT  GCC  AAG  GTG  GAA  GAA  GCC  AAG  GAG  AAA  GTG  ACT      360
Val  Lys  Pro  Val  Ala  Lys  Val  Glu  Glu  Ala  Lys  Glu  Lys  Val  Thr
          110                 115                      120

GTG  AAA  CCA  TTC  CCT  GAG  GTG  ATG  GGG  ATC  ACA  AAT  ACA  ACA  GCA      405
Val  Lys  Pro  Phe  Pro  Glu  Val  MET  Gly  Ile  Thr  Asn  Thr  Thr  Ala
     125                      130                      135

TCA  ACA  GCC  TCT  GTG  GTG  GAG  AGA  ACA  AAG  GAG  AAA  ACA  ACA  GCG      450
Ser  Thr  Ala  Ser  Val  Val  Glu  Arg  Thr  Lys  Glu  Lys  Thr  Thr  Ala
140                      145                      150

AGA  CCA  GTT  CCA  GGG  GTG  GGG  GAA  GCT  GAT  GGG  AAG  AGA  ACA  ACG      495
Arg  Pro  Val  Pro  Gly  Val  Gly  Glu  Ala  Asp  Gly  Lys  Arg  Thr  Thr
               155                      160                      165

ATA  GCA  CTT  CCC  AGC  ATG  AAG  GAA  GAC  AAA  GAG  AAG  GCG  ACT  GTG      540
Ile  Ala  Leu  Pro  Ser  MET  Lys  Glu  Asp  Lys  Glu  Lys  Ala  Thr  Val
                    170                      175                      180

AAA  CCA  TCC  TTT  GGG  ATG  AAG  GTA  GCT  CAT  GCA  AAC  AGC  ACA  TCC      585
Lys  Pro  Ser  Phe  Gly  MET  Lys  Val  Ala  His  Ala  Asn  Ser  Thr  Ser
                         185                      190                      195

AAA  GAT  AAA  CCA  AAG  GCA  GAA  GAG  CCT  CCT  GCA  TCA  GTG  AAA  GCC      630
Lys  Asp  Lys  Pro  Lys  Ala  Glu  Glu  Pro  Pro  Ala  Ser  Val  Lys  Ala
                              200                      205                      210

ATA  AGA  CCT  GTG  ACT  CAG  GCT  GCC  ACA  GTG  ACA  GAG  AAG  AAG  AAA      675
Ile  Arg  Pro  Val  Thr  Gln  Ala  Ala  Thr  Val  Thr  Glu  Lys  Lys  Lys
                    215                      220                      225

CTG  AGG  GCT  GCT  GAC  TTC  AAG  ACT  GAG  CCA  CAG  TGG  GAT  TTT  GAT      720
Leu  Arg  Ala  Ala  Asp  Phe  Lys  Thr  Glu  Pro  Gln  Trp  Asp  Phe  Asp
               230                      235                      240

GAT  GAG  TAC  ATA  CTG  GAT  AGC  TCA  TCT  CCA  GTA  TCG  ACC  TGC  TCT      765
Asp  Glu  Tyr  Ile  Leu  Asp  Ser  Ser  Ser  Pro  Val  Ser  Thr  Cys  Ser
          245                      250                      255

GAA  TCA  GTG  AGA  GCC  AAG  GCT  GCC  AAG  TCT  GAC  TGG  CTG  CGA  GAT      810
Glu  Ser  Val  Arg  Ala  Lys  Ala  Ala  Lys  Ser  Asp  Trp  Leu  Arg  Asp
                    260                      265                      270

CTT  TTC  CTG  CCG  AAC  ATC  ACA  CTC  TTC  ATA  GAC  AAG  AGT  TAC  TTC      855
Leu  Phe  Leu  Pro  Asn  Ile  Thr  Leu  Phe  Ile  Asp  Lys  Ser  Tyr  Phe
               275                      280                      285

AAT  GTC  AGT  GAG  TGG  GAC  CGC  CTG  GAG  CAT  TTT  GCA  CCT  CCC  TAT      900
Asn  Val  Ser  Glu  Trp  Asp  Arg  Leu  Glu  His  Phe  Ala  Pro  Pro  Tyr
                         290                      295                      300

GGC  TTC  ATG  GAG  CTG  AAT  TAC  TCA  CTG  GTA  GAA  GAA  GTC  ATG  TCA      945
Gly  Phe  MET  Glu  Leu  Asn  Tyr  Ser  Leu  Val  Glu  Glu  Val  MET  Ser
                              305                      310                      315

CGG  CTG  CCT  CCA  AAT  CCC  CAC  CAG  CAG  CTG  CTC  CTG  GCC  AAC  AGT      990
Arg  Leu  Pro  Pro  Asn  Pro  His  Gln  Gln  Leu  Leu  Leu  Ala  Asn  Ser
                    320                      325                      330

AGC  AGC  AAC  GTG  TCA  ACG  TGC  ATC  AGC  TGT  GCT  GTT  GTG  GGG  AAT     1035
Ser  Ser  Asn  Val  Ser  Thr  Cys  Ile  Ser  Cys  Ala  Val  Val  Gly  Asn
                         335                      340                      345

GGA  GGG  ATA  TTG  AAT  AAC  TCT  GGA  ATG  GGC  CAG  GAG  ATT  GAC  TCC     1080
Gly  Gly  Ile  Leu  Asn  Asn  Ser  Gly  MET  Gly  Gln  Glu  Ile  Asp  Ser
                              350                      355                      360

CAT  GAC  TAT  GTG  TTC  CGG  GTG  AGC  GGG  GCT  GTA  ATC  AAA  GGT  TAC     1125
His  Asp  Tyr  Val  Phe  Arg  Val  Ser  Gly  Ala  Val  Ile  Lys  Gly  Tyr
                    365                      370                      375

GAA  AAG  GAT  GTG  GGA  ACA  AAA  ACC  TCC  TTC  TAC  GGA  TTC  ACA  GCG     1170
Glu  Lys  Asp  Val  Gly  Thr  Lys  Thr  Ser  Phe  Tyr  Gly  Phe  Thr  Ala
                    380                      385                      390

TAC  TCC  CTG  GTG  TCC  TCT  CTC  CAG  AAC  TTG  GGA  CAC  AAA  GGG  TTC     1215
Tyr  Ser  Leu  Val  Ser  Ser  Leu  Gln  Asn  Leu  Gly  His  Lys  Gly  Phe
                    395                      400                      405
```

```
AAG AAG ATC CCA CAG GGG AAG CAT ATC AGA TAC ATT CAC TTC CTG            1260
Lys Lys Ile Pro Gln Gly Lys His Ile Arg Tyr Ile His Phe Leu
        410                 415                 420

GAG GCA GTT AGA GAC TAT GAG TGG CTG AAG GCT CTT CTG TTG GAC            1305
Glu Ala Val Arg Asp Tyr Glu Trp Leu Lys Ala Leu Leu Leu Asp
425                 430                 435

AAG GAT ATC AGG AAA GGA TTC CTG AAC TAC TAT GGG CGA AGG CCC            1350
Lys Asp Ile Arg Lys Gly Phe Leu Asn Tyr Tyr Gly Arg Arg Pro
        440                 445                 450

CGG GAG AGA TTC GAT GAA GAT TTC ACA ATG AAT AAG TAC CTG GTA            1395
Arg Glu Arg Phe Asp Glu Asp Phe Thr MET Asn Lys Tyr Leu Val
        455                 460                 465

GCT CAC CCT GAT TTC CTC AGA TAC TTG AAA AAC AGG TTC TTA AAA            1440
Ala His Pro Asp Phe Leu Arg Tyr Leu Lys Asn Arg Phe Leu Lys
        470                 475                 480

TCT AAA AAT CTG CAA AAG CCC TAC TGG CGG CTG TAC AGA CCC ACA            1485
Ser Lys Asn Leu Gln Lys Pro Tyr Trp Arg Leu Tyr Arg Pro Thr
        485                 490                 495

ACA GGA GCC CTC CTG CTG CTG ACT GCC CTG CAT CTC TGT GAC CGG            1530
Thr Gly Ala Leu Leu Leu Leu Thr Ala Leu His Leu Cys Asp Arg
        500                 505                 510

GTG AGT GCC TAT GGC TAC ATC ACA GAA GGT CAC CAG AAG TAC TCG            1575
Val Ser Ala Tyr Gly Tyr Ile Thr Glu Gly His Gln Lys Tyr Ser
        515                 520                 525

GAT CAC TAC TAT GAC AAG GAG TGG AAA CGC CTG GTC TTC TAC GTT            1620
Asp His Tyr Tyr Asp Lys Glu Trp Lys Arg Leu Val Phe Tyr Val
        530                 535                 540

AAC CAT GAC TTC AAC TTG GAG AAG CAG GTG TGG AAA AGG CTT CAT            1665
Asn His Asp Phe Asn Leu Glu Lys Gln Val Trp Lys Arg Leu His
        545                 550                 555

GAT GAG AAC ATC ATG AAG CTC TAC CAG AGA TCC TGA CAG TGT GCC            1710
Asp Glu Asn Ile MET Lys Leu Tyr Gln Arg Ser
        560                 565

GAGGGCCATT GCCTGGGAAA TCTCAACAGC ACCTCATGGG GAACAGAAGA            1760
        GGACCTCGGA AGCCAGGGTT AGCTCTGGAC TTCCAGGCCC AGCTTCAGCT            1810
        CCACAGAGAT ATTTCCCTCC TTTGATATCT TTATTTTCTC ACAACACTTC            1860
        CTAAAATGTG CATATTCTAC AGACCAAGCG AACAGTAGGG AAAAGTGCCT            1910
        CCAAACAAGG TCCCATCTGA CTTGTGGACG GTTGTAGGCT CTGGTACTGG            1960
        GAAAGAGGAA TCCGGGATGA ATCCGAATAG CAGATGTTCC AGTGCCCATT            2010
        ATCTTAATCA GGTTCTCCCT CTGCAAGGAG ATGCTCTTGG GCTGGGGCT             2060
        AGTTTGCTC TAGGTGGGTT CTCTCTGTGA GTAGTGCTTG TTATGGAGCT             2110
        GGGTGTTTTG GGTAAGCAGT GGATAGAATG GAGACACACA CAATCCTGTC            2160
        TCAAGAGGAT GATTTGTGTC CTGGAGGTGC TGCTGTCACT CTGCTCACTG            2210
        CAGGCATAAG GACCCTTCCA ATGAACTCAA TCCCAATGTG ACTTTGCTGT            2260
        GACACCTCCT GGGGAGCACT GTGATGTCGG TGCCCAGCCT GCTGCCCTTG            2310
        GCCTAGTTCA CCATCAGCAC AAGGGAAGGG GAGAGCCCTC CGTAGTGCAG            2360
        CAGAATGCTG GACATTGTAC CTCTTGCTGT GGGTTCCCCT GGCTGCAGAC            2410
        TACGTGTAGT GAGTCTGATG AAGAAGCTGG TGCTTGGCTG TGCCAGGAGC            2460
        ATGGTGCTTC CTCTTCTACC AGGAGAAATG AGAATTCTCA ATGTCCATGG            2510
        ATGGATGCTG TCTGTCCTTG CTGCTGGCTG GAGTGCCTGC CTACATTGTC            2560
        CTGAGAAAAG CACTGTTACA GCCAGTAAGC CTTTGGAGTA TTGGCCTTCT            2610
```

-continued

| GAGTGGGCTT | TTGCAAACAA | AATAAACGGC | ACTGCTTTCC | CCCAAGCTGA | 2660 |
| AAAAAAAAAA | A | | | | 2671 |

( 2 ) INFORMATION FOR SEQ ID NO:2:

( i ) SEQUENCE CHARACTERISTICS:
    ( A ) LENGTH: 1206
    ( B ) TYPE: nucleic acid
    ( C ) STRANDEDNESS: double
    ( D ) TOPOLOGY: linear ( i i ) MOLECULE TYPE: cDNA to mRNA ( x i ) SEQUENCE DESCRIPTION: SEQ ID NO:2:

| ATG | AAA | TTC | AGC | TGG | GTC | ATG | TTC | TTC | CTG | ATG | GCA | GTG | GTT | ACA | 45 |
| MET | Lys | Phe | Ser | Trp | Val | MET | Phe | Phe | Leu | MET | Ala | Val | Val | Thr | |
| 1 | | | | 5 | | | | | 10 | | | | | 15 | |
| GGG | GTC | AAT | TCA | GAA | TTC | ACT | GAG | CCA | CAG | TGG | GAT | TTT | GAT | GAT | 90 |
| Gly | Val | Asn | Ser | Glu | Phe | Thr | Glu | Pro | Gln | Trp | Asp | Phe | Asp | Asp | |
| | | | | 20 | | | | | 25 | | | | | 30 | |
| GAG | TAC | ATA | CTG | GAT | AGC | TCA | TCT | CCA | GTA | TCG | ACC | TGC | TCT | GAA | 135 |
| Glu | Tyr | Ile | Leu | Asp | Ser | Ser | Ser | Pro | Val | Ser | Thr | Cys | Ser | Glu | |
| | | | | 35 | | | | | 40 | | | | | 45 | |
| TCA | GTG | AGA | GCC | AAG | GCT | GCC | AAG | TCT | GAC | TGG | CTG | CGA | GAT | CTT | 180 |
| Ser | Val | Arg | Ala | Lys | Ala | Ala | Lys | Ser | Asp | Trp | Leu | Arg | Asp | Leu | |
| | | | | 50 | | | | | 55 | | | | | 60 | |
| TTC | CTG | CCG | AAC | ATC | ACA | CTC | TTC | ATA | GAC | AAG | AGT | TAC | TTC | AAT | 225 |
| Phe | Leu | Pro | Asn | Ile | Thr | Leu | Phe | Ile | Asp | Lys | Ser | Tyr | Phe | Asn | |
| | | | | 65 | | | | | 70 | | | | | 75 | |
| GTC | AGT | GAG | TGG | GAC | CGC | CTG | GAG | CAT | TTT | GCA | CCT | CCC | TAT | GGC | 270 |
| Val | Ser | Glu | Trp | Asp | Arg | Leu | Glu | His | Phe | Ala | Pro | Pro | Tyr | Gly | |
| | | | | 80 | | | | | 85 | | | | | 90 | |
| TTC | ATG | GAG | CTG | AAT | TAC | TCA | CTG | GTA | GAA | GAA | GTC | ATG | TCA | CGG | 315 |
| Phe | MET | Glu | Leu | Asn | Tyr | Ser | Leu | Val | Glu | Glu | Val | MET | Ser | Arg | |
| | | | | 95 | | | | | 100 | | | | | 105 | |
| CTG | CCT | CCA | AAT | CCC | CAC | CAG | CAG | CTG | CTC | CTG | GCC | AAC | AGT | AGC | 360 |
| Leu | Pro | Pro | Asn | Pro | His | Gln | Gln | Leu | Leu | Leu | Ala | Asn | Ser | Ser | |
| | | | | 110 | | | | | 115 | | | | | 120 | |
| AGC | AAC | GTG | TCA | ACG | TGC | ATC | AGC | TGT | GCT | GTT | GTG | GGG | AAT | GGA | 405 |
| Ser | Asn | Val | Ser | Thr | Cys | Ile | Ser | Cys | Ala | Val | Val | Gly | Asn | Gly | |
| | | | | 125 | | | | | 130 | | | | | 135 | |
| GGG | ATA | TTG | AAT | AAC | TCT | GGA | ATG | GGC | CAG | GAG | ATT | GAC | TCC | CAT | 450 |
| Gly | Ile | Leu | Asn | Asn | Ser | Gly | MET | Gly | Gln | Glu | Ile | Asp | Ser | His | |
| | | | | 140 | | | | | 145 | | | | | 150 | |
| GAC | TAT | GTG | TTC | CGG | GTG | AGC | GGG | GCT | GTA | ATC | AAA | GGT | TAC | GAA | 495 |
| Asp | Tyr | Val | Phe | Arg | Val | Ser | Gly | Ala | Val | Ile | Lys | Gly | Tyr | Glu | |
| | | | | 155 | | | | | 160 | | | | | 165 | |
| AAG | GAT | GTG | GGA | ACA | AAA | ACC | TCC | TTC | TAC | GGA | TTC | ACA | GCG | TAC | 540 |
| Lys | Asp | Val | Gly | Thr | Lys | Thr | Ser | Phe | Tyr | Gly | Phe | Thr | Ala | Tyr | |
| | | | | 170 | | | | | 175 | | | | | 180 | |
| TCC | CTG | GTG | TCC | TCT | CTC | CAG | AAC | TTG | GGA | CAC | AAA | GGG | TTC | AAG | 585 |
| Ser | Leu | Val | Ser | Ser | Leu | Gln | Asn | Leu | Gly | His | Lys | Gly | Phe | Lys | |
| | | | | 185 | | | | | 190 | | | | | 195 | |
| AAG | ATC | CCA | CAG | GGG | AAG | CAT | ATC | AGA | TAC | ATT | CAC | TTC | CTG | GAG | 630 |
| Lys | Ile | Pro | Gln | Gly | Lys | His | Ile | Arg | Tyr | Ile | His | Phe | Leu | Glu | |
| | | | | 200 | | | | | 205 | | | | | 210 | |
| GCA | GTT | AGA | GAC | TAT | GAG | TGG | CTG | AAG | GCT | CTT | CTG | TTG | GAC | AAG | 675 |
| Ala | Val | Arg | Asp | Tyr | Glu | Trp | Leu | Lys | Ala | Leu | Leu | Leu | Asp | Lys | |
| | | | | 215 | | | | | 220 | | | | | 225 | |
| GAT | ATC | AGG | AAA | GGA | TTC | CTG | AAC | TAC | TAT | GGG | CGA | AGG | CCC | CGG | 720 |
| Asp | Ile | Arg | Lys | Gly | Phe | Leu | Asn | Tyr | Tyr | Gly | Arg | Arg | Pro | Arg | |

|   |   |   |   |   |   |   | 230 |   |   |   |   | 235 |   |   |   |   | 240 |   |   |      |
|---|---|---|---|---|---|---|-----|---|---|---|---|-----|---|---|---|---|-----|---|---|------|
| GAG | AGA | TTC | GAT | GAA | GAT | TTC | ACA | ATG | AAT | AAG | TAC | CTG | GTA | GCT |   |   |   |   |   | 765 |
| Glu | Arg | Phe | Asp | Glu | Asp | Phe | Thr | MET | Asn | Lys | Tyr | Leu | Val | Ala |   |   |   |   |   |      |
|     |     |     |     | 245 |     |     |     | 250 |     |     |     |     |     | 255 |   |   |   |   |   |      |

```
CAC  CCT  GAT  TTC  CTC  AGA  TAC  TTG  AAA  AAC  AGG  TTC  TTA  AAA  TCT              810
His  Pro  Asp  Phe  Leu  Arg  Tyr  Leu  Lys  Asn  Arg  Phe  Leu  Lys  Ser
               260                      265                      270

AAA  AAT  CTG  CAA  AAG  CCC  TAC  TGG  CGG  CTG  TAC  AGA  CCC  ACA  ACA              855
Lys  Asn  Leu  Gln  Lys  Pro  Tyr  Trp  Arg  Leu  Tyr  Arg  Pro  Thr  Thr
               275                      280                      285

GGA  GCC  CTC  CTG  CTG  CTG  ACT  GCC  CTG  CAT  CTC  TGT  GAC  CGG  GTG              900
Gly  Ala  Leu  Leu  Leu  Leu  Thr  Ala  Leu  His  Leu  Cys  Asp  Arg  Val
               290                      295                      300

AGT  GCC  TAT  GGC  TAC  ATC  ACA  GAA  GGT  CAC  CAG  AAG  TAC  TCG  GAT              945
Ser  Ala  Tyr  Gly  Tyr  Ile  Thr  Glu  Gly  His  Gln  Lys  Tyr  Ser  Asp
               305                      310                      315

CAC  TAC  TAT  GAC  AAG  GAG  TGG  AAA  CGC  CTG  GTC  TTC  TAC  GTT  AAC              990
His  Tyr  Tyr  Asp  Lys  Glu  Trp  Lys  Arg  Leu  Val  Phe  Tyr  Val  Asn
               320                      325                      330

CAT  GAC  TTC  AAC  TTG  GAG  AAG  CAG  GTG  TGG  AAA  AGG  CTT  CAT  GAT             1035
His  Asp  Phe  Asn  Leu  Glu  Lys  Gln  Val  Trp  Lys  Arg  Leu  His  Asp
               335                      340                      345

GAG  AAC  ATC  ATG  AAG  CTC  TAC  CAG  AGA  TCC  TGA  CAGTGTGCCGA G                   1080
Glu  Asn  Ile  MET  Lys  Leu  Tyr  Gln  Arg  Ser
               350                      355

GGCCATTGCC  TGGGAAATCT  CAACAGCACC  TCATGGGGAA  CAGAAGAGGA                       1130

CCTCGGAAGC  CAGGGTTAGC  TCTGGACTTC  CAGGCCCAGC  TTCAGCTCCA                       1180

CAGAGATATT  TCCCTCCTTT  GATATC                                                    1206
```

( 2 ) INFORMATION FOR SEQ ID NO:3:

( i ) SEQUENCE CHARACTERISTICS:
        ( A ) LENGTH: 1666
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: G. gallus (chicken)

( i x ) FEATURE:
        ( D ) OTHER INFORMATION: CDS 1- 1212

( x i ) SEQUENCE DESCRIPTION: SEQ ID NO:3:

```
ATG  GGT  TCC  CCC  CGC  TGG  AAG  CGT  TTC  TGC  TTC  TTG  CTC  CTC  GCA               45
MET  Gly  Ser  Pro  Arg  Trp  Lys  Arg  Phe  Cys  Phe  Leu  Leu  Leu  Ala
 1                  5                        10                       15

GCC  TTC  ACC  TCG  TCC  CTT  CTG  CTC  TAC  GGG  CAC  TAC  TAC  GCT  ACG               90
Ala  Phe  Thr  Ser  Ser  Leu  Leu  Leu  Tyr  Gly  His  Tyr  Tyr  Ala  Thr
                    20                       25                       30

GTG  GAC  GTG  CGC  AGC  GGC  CCG  AGG  GTC  GTG  ACC  AGC  CTG  CTG  CAG              135
Val  Asp  Val  Arg  Ser  Gly  Pro  Arg  Val  Val  Thr  Ser  Leu  Leu  Gln
                    35                       40                       45

CCA  GAG  CTG  CTG  TTC  CTG  GTC  CGC  CCA  GAC  ACC  CCA  CAC  CCA  GAC              180
Pro  Glu  Leu  Leu  Phe  Leu  Val  Arg  Pro  Asp  Thr  Pro  His  Pro  Asp
                    50                       55                       60

AAC  AGC  CAC  CAC  AAG  GAG  CTC  AGA  GGG  ACT  GTG  AAG  AGC  AGG  GAG              225
Asn  Ser  His  His  Lys  Glu  Leu  Arg  Gly  Thr  Val  Lys  Ser  Arg  Glu
                    65                       70                       75

TTC  TTC  TCC  CAA  CCA  TCC  TCA  GAG  CTG  GAG  AAG  CCC  AAA  CCC  AGT              270
```

|     |     |     |     |     |     |     |     |     |     |     |     |     |     |     |     |      |
|---|---|---|---|---|---|---|---|---|---|---|---|---|---|---|---|---|
| Phe | Phe | Ser | Gln | Pro | Ser | Ser | Glu | Leu | Glu | Lys | Pro | Lys | Pro | Ser | | |
|     |     |     |     | 80  |     |     |     |     | 85  |     |     |     |     | 90  | | |
| GGA | AAG | CAG | CCC | ACC | CCG | TGC | CCC | CGC | TCG | GTG | GCA | GCC | ACG | GCG | | 315 |
| Gly | Lys | Gln | Pro | Thr | Pro | Cys | Pro | Arg | Ser | Val | Ala | Ala | Thr | Ala | | |
|     |     |     |     | 95  |     |     |     |     | 100 |     |     |     |     | 105 | | |
| AAG | GCA | GAC | CCC | ACG | TTT | GGG | GAG | CTC | TTC | CAA | TTT | GAC | ATC | CCG | | 360 |
| Lys | Ala | Asp | Pro | Thr | Phe | Gly | Glu | Leu | Phe | Gln | Phe | Asp | Ile | Pro | | |
|     |     |     |     | 110 |     |     |     |     | 115 |     |     |     |     | 120 | | |
| GTG | CTG | ATG | TGG | GAC | CAA | CAC | TTC | AAC | CCT | GAG | ACG | TGG | GAC | AGG | | 405 |
| Val | Leu | Met | Trp | Asp | Gln | His | Phe | Asn | Pro | Glu | Thr | Trp | Asp | Arg | | |
|     |     |     |     | 125 |     |     |     |     | 130 |     |     |     |     | 135 | | |
| CTG | AAG | GCA | CGA | CGC | GTC | CCA | TAC | GGC | TGG | CAG | GGT | TTG | TCC | CAA | | 450 |
| Leu | Lys | Ala | Arg | Arg | Val | Pro | Tyr | Gly | Trp | Gln | Gly | Leu | Ser | Gln | | |
|     |     |     |     | 140 |     |     |     |     | 145 |     |     |     |     | 150 | | |
| GCA | GCT | GTC | GGC | AGC | ACC | CTG | CGT | CTC | CTT | AAC | ACC | TCC | TCC | AAC | | 495 |
| Ala | Ala | Val | Gly | Ser | Thr | Leu | Arg | Leu | Leu | Asn | Thr | Ser | Ser | Asn | | |
|     |     |     |     | 155 |     |     |     |     | 160 |     |     |     |     | 165 | | |
| ACG | CGG | CTC | TTC | GAC | CGC | CAC | CTC | TTC | CCC | GGG | GGC | TGC | ATC | CGC | | 540 |
| Thr | Arg | Leu | Phe | Asp | Arg | His | Leu | Phe | Pro | Gly | Gly | Cys | Ile | Arg | | |
|     |     |     |     | 170 |     |     |     |     | 175 |     |     |     |     | 180 | | |
| TGT | GCC | GTG | GTG | GGC | AAT | GGG | GGA | ATC | CTC | AAC | GGC | TCA | CGG | CAG | | 585 |
| Cys | Ala | Val | Val | Gly | Asn | Gly | Gly | Ile | Leu | Asn | Gly | Ser | Arg | Gln | | |
|     |     |     |     | 185 |     |     |     |     | 190 |     |     |     |     | 195 | | |
| GGC | CGG | GCC | ATC | GAC | GCA | CAT | GAT | TTG | GTC | TTC | AGG | CTG | AAC | GGG | | 630 |
| Gly | Arg | Ala | Ile | Asp | Ala | His | Asp | Leu | Val | Phe | Arg | Leu | Asn | Gly | | |
|     |     |     |     | 200 |     |     |     |     | 205 |     |     |     |     | 210 | | |
| GCC | ATC | ACC | AAA | GGC | TTT | GAG | GAG | GAT | GTT | GGG | AGC | AAG | GTT | TCG | | 675 |
| Ala | Ile | Thr | Lys | Gly | Phe | Glu | Glu | Asp | Val | Gly | Ser | Lys | Val | Ser | | |
|     |     |     |     | 215 |     |     |     |     | 220 |     |     |     |     | 225 | | |
| TTC | TAC | GGC | TTC | ACG | GTG | AAC | ACC | ATG | AAG | AAC | TCA | CTC | ATT | GCC | | 720 |
| Phe | Tyr | Gly | Phe | Thr | Val | Asn | Thr | Met | Lys | Asn | Ser | Leu | Ile | Ala | | |
|     |     |     |     | 230 |     |     |     |     | 235 |     |     |     |     | 240 | | |
| TAT | GAG | GCG | TAT | GGC | TTC | ACC | CGG | ACA | CCG | CAG | GGC | AAG | GAC | CTG | | 765 |
| Tyr | Glu | Ala | Tyr | Gly | Phe | Thr | Arg | Thr | Pro | Gln | Gly | Lys | Asp | Leu | | |
|     |     |     |     | 245 |     |     |     |     | 250 |     |     |     |     | 255 | | |
| AAG | TAC | ATC | TTC | ATC | CCC | TCG | GAC | GCA | CGC | GAC | TAC | ATC | ATG | CTG | | 810 |
| Lys | Tyr | Ile | Phe | Ile | Pro | Ser | Asp | Ala | Arg | Asp | Tyr | Ile | Met | Leu | | |
|     |     |     |     | 260 |     |     |     |     | 265 |     |     |     |     | 270 | | |
| AGG | TCG | GCC | ATT | CAG | GGC | AGC | CCA | GTC | CCC | GAG | GGC | TTG | GAC | AAG | | 855 |
| Arg | Ser | Ala | Ile | Gln | Gly | Ser | Pro | Val | Pro | Glu | Gly | Leu | Asp | Lys | | |
|     |     |     |     | 275 |     |     |     |     | 280 |     |     |     |     | 285 | | |
| GGC | GAC | GAG | CCA | CAG | AAG | TAT | TTT | GGA | CTG | GAG | GCA | TCT | GCG | GAG | | 900 |
| Gly | Asp | Glu | Pro | Gln | Lys | Tyr | Phe | Gly | Leu | Glu | Ala | Ser | Ala | Glu | | |
|     |     |     |     | 290 |     |     |     |     | 295 |     |     |     |     | 300 | | |
| AAG | TTC | AAG | CTG | CTG | CAT | CCC | GAT | TTC | TTG | CAT | TAC | CTG | ACA | ACC | | 945 |
| Lys | Phe | Lys | Leu | Leu | His | Pro | Asp | Phe | Leu | His | Tyr | Leu | Thr | Thr | | |
|     |     |     |     | 305 |     |     |     |     | 310 |     |     |     |     | 315 | | |
| AGG | TTC | CTG | AGG | TCA | GAG | CTC | CTG | GAC | ATG | CAG | TAC | GGC | CAC | CTC | | 990 |
| Arg | Phe | Leu | Arg | Ser | Glu | Leu | Leu | Asp | Met | Gln | Tyr | Gly | His | Leu | | |
|     |     |     |     | 320 |     |     |     |     | 325 |     |     |     |     | 330 | | |
| TAC | ATG | CCC | AGC | ACT | GGG | GCA | CTC | ATG | CTG | CTG | ACA | GCA | CTG | CAC | | 1035 |
| Tyr | Met | Pro | Ser | Thr | Gly | Ala | Leu | Met | Leu | Leu | Thr | Ala | Leu | His | | |
|     |     |     |     | 335 |     |     |     |     | 340 |     |     |     |     | 345 | | |
| ACC | TGC | GAC | CAG | GTC | AGT | GCC | TAC | GGG | TTC | ATC | ACA | GCC | AAC | TAC | | 1080 |
| Thr | Cys | Asp | Gln | Val | Ser | Ala | Tyr | Gly | Phe | Ile | Thr | Ala | Asn | Tyr | | |
|     |     |     |     | 350 |     |     |     |     | 355 |     |     |     |     | 360 | | |
| GAG | CAG | TTC | TCC | GAC | CAT | TAC | TAC | GAG | CCA | GAG | AAG | AAG | CCA | CTG | | 1125 |
| Glu | Gln | Phe | Ser | Asp | His | Tyr | Tyr | Glu | Pro | Glu | Lys | Lys | Pro | Leu | | |
|     |     |     |     | 365 |     |     |     |     | 370 |     |     |     |     | 375 | | |
| GTG | TTC | TAC | GCC | AAC | CAC | GAC | ATG | CTG | CTG | GAA | GCA | GAG | CTG | TGG | | 1170 |

|  |  |  |  |  |  |  |  |  |  |  |  |  |  |
|---|---|---|---|---|---|---|---|---|---|---|---|---|---|
| Val | Phe | Tyr | Ala | Asn<br>380 | His | Asp | Met | Leu | Leu<br>385 | Glu | Ala | Glu | Leu | Trp<br>390 |

| AGG | AGT | TTG | CAC | CGG | GCG | GGG | ATC | ATG | GAG | CTG | TAC | CAG | CGG | TGA | 1215 |
|---|---|---|---|---|---|---|---|---|---|---|---|---|---|---|---|
| Arg | Ser | Leu | His<br>395 | Arg | Ala | Gly | Ile | Met | Glu<br>400 | Leu | Tyr | Gln | Arg | | |

| GGGCAGCGCA | GTCCCACTGC | AAGGACTCTC | AATGCAACGC | AGAAGCGGTT | CTCCTCTTTC | 1275 |
|---|---|---|---|---|---|---|
| CTGAAGGCCT | CCTTCTGTCC | CTGGAGGGCT | CTCCCACACT | GGCGGGCCAG | CCTGAGGAGC | 1335 |
| AGGGCCTGCA | GCTGACAGCA | GAGCAAAGGT | GGTGGTGCAG | GGCGAGCCAA | GGCTGGCAGG | 1395 |
| GAAATACTGC | AACTCCTCAG | GGCCCTTCAG | CATCTTATTT | GTGACTCTGA | GACTGAGCAC | 1455 |
| GGCCTTGGGG | AGCCTCCGCA | CGTGGCTGTG | AGCTCCTGAT | GCCATGAGAA | TGTCTGTGGG | 1515 |
| GTGGCAGCAG | CCCCTGGGAA | GCACAGTGTT | CATGTGCAGG | TGGGGCACAG | TGGTGCTGGA | 1575 |
| AGGGGATGCT | GGAGAAGCAT | ACATCTGACA | GACCTCACTT | CTTGGAACTT | CCTGGAGTTG | 1635 |
| CAGCCTCGAA | GTCACGCTGG | GTAGGCTGCA | G | | | 1666 |

( 2 ) INFORMATION FOR SEQ ID NO:4:

( i ) SEQUENCE CHARACTERISTICS:
        ( A ) LENGTH: 1146
        ( B ) TYPE: nucleic acid
        ( C ) STRANDEDNESS: double
        ( D ) TOPOLOGY: linear ( i i ) MOLECULE TYPE: DNA ( v i ) ORIGINAL SOURCE:
        ( A ) ORGANISM: mouse ( i x ) FEATURE:
        ( D ) OTHER INFORMATION: 1-1128 sialyltransferase in soluble
           form ( x i ) SEQUENCE DESCRIPTION: SEQ ID NO:4:

| ATG | GGG | AGC | GAC | TAT | GAG | GCT | CTT | ACA | TTG | CAA | GCC | AAG | GTA | TTC | 45 |
|---|---|---|---|---|---|---|---|---|---|---|---|---|---|---|---|
| MET<br>1 | Gly | Ser | Asp | Tyr<br>5 | Glu | Ala | Leu | Thr | Leu<br>10 | Gln | Ala | Lys | Val | Phe<br>15 | |

| CAG | ATG | CCG | AAG | AGC | CAG | GAG | AAA | GTG | GCC | GTG | GGG | CCT | GCT | CCC | 90 |
|---|---|---|---|---|---|---|---|---|---|---|---|---|---|---|---|
| Gln | MET | Pro | Lys | Ser<br>20 | Gln | Glu | Lys | Val | Ala<br>25 | Val | Gly | Pro | Ala | Pro<br>30 | |

| CAG | GCT | GTG | TTC | TCA | AAC | AGC | AAA | CAA | GAC | CCT | AAG | GAA | GGC | GTT | 135 |
|---|---|---|---|---|---|---|---|---|---|---|---|---|---|---|---|
| Gln | Ala | Val | Phe | Ser<br>35 | Asn | Ser | Lys | Gln | Asp<br>40 | Pro | Lys | Glu | Gly | Val<br>45 | |

| CAG | ATC | CTC | AGT | TAC | CCC | AGG | GTC | ACA | GCC | AAG | GTC | AAG | CCA | CAG | 180 |
|---|---|---|---|---|---|---|---|---|---|---|---|---|---|---|---|
| Gln | Ile | Leu | Ser | Tyr<br>50 | Pro | Arg | Val | Thr | Ala<br>55 | Lys | Val | Lys | Pro | Gln<br>60 | |

| CCC | TCC | TTG | CAG | GTG | TGG | GAC | AAG | GAC | TCC | ACA | TAC | TCA | AAA | CTT | 225 |
|---|---|---|---|---|---|---|---|---|---|---|---|---|---|---|---|
| Pro | Ser | Leu | Gln | Val<br>65 | Trp | Asp | Lys | Asp | Ser<br>70 | Thr | Tyr | Ser | Lys | Leu<br>75 | |

| AAC | CCC | AGG | CTG | CTG | AAG | ATC | TGG | AGG | AAC | TAT | CTG | AAC | ATG | AAT | 270 |
|---|---|---|---|---|---|---|---|---|---|---|---|---|---|---|---|
| Asn | Pro | Arg | Leu | Leu<br>80 | Lys | Ile | Trp | Arg | Asn<br>85 | Tyr | Leu | Asn | MET | Asn<br>90 | |

| AAA | TAT | AAA | GTG | TCC | TAC | AAG | GGG | CCG | GGA | CCA | GGA | GTC | AGG | TTC | 315 |
|---|---|---|---|---|---|---|---|---|---|---|---|---|---|---|---|
| Lys | Tyr | Lys | Val | Ser<br>95 | Tyr | Lys | Gly | Pro | Gly<br>100 | Pro | Gly | Val | Arg | Phe<br>105 | |

| AGC | GTA | GAA | GGC | CTG | CGC | TGC | CAC | CTT | CGA | GAC | CAC | GTG | AAT | GTG | 360 |
|---|---|---|---|---|---|---|---|---|---|---|---|---|---|---|---|
| Ser | Val | Glu | Gly | Leu<br>110 | Arg | Cys | His | Leu | Arg<br>115 | Asp | His | Val | Asn | Val<br>120 | |

| TCT | ATG | ATA | GAG | GCC | ACA | GAT | TCT | CCC | TTC | AAC | ACC | ACT | GAA | TGG | 405 |
|---|---|---|---|---|---|---|---|---|---|---|---|---|---|---|---|
| Ser | MET | Ile | Glu | Ala<br>125 | Thr | Asp | Ser | Pro | Phe<br>130 | Asn | Thr | Thr | Glu | Trp<br>135 | |

| GAG | GGT | TAC | CTG | CCC | AAA | GAG | ACA | TTC | AGA | ACC | AAG | GCT | GGG | CCT | 450 |

```
Glu  Gly  Tyr  Leu  Pro  Lys  Glu  Thr  Phe  Arg  Thr  Lys  Ala  Gly  Pro
          140                      145                      150

TGC  ACA  AAG  TGT  GCC  GTC  GTG  TCT  TCT  GCA  GGA  TCT  CTG  AAG  AAC         495
Cys  Thr  Lys  Cys  Ala  Val  Val  Ser  Ser  Ala  Gly  Ser  Leu  Lys  Asn
          155                      160                      165

TCC  CAG  CTG  GGT  CGA  GAG  ATT  GAT  AAT  CAT  GAT  GCG  GTC  CTG  AGG         540
Ser  Gln  Leu  Gly  Arg  Glu  Ile  Asp  Asn  His  Asp  Ala  Val  Leu  Arg
          170                      175                      180

TTT  AAT  GGG  GCA  CCT  ACA  GAC  AAC  TTC  CAA  CAG  GAT  GTG  GGC  ACA         585
Phe  Asn  Gly  Ala  Pro  Thr  Asp  Asn  Phe  Gln  Gln  Asp  Val  Gly  Thr
          185                      190                      195

AAA  ACT  ACC  ATC  CGC  CTA  GTG  AAC  TCT  CAG  TTA  GTC  ACC  ACA  GAA         630
Lys  Thr  Thr  Ile  Arg  Leu  Val  Asn  Ser  Gln  Leu  Val  Thr  Thr  Glu
          200                      205                      210

AAG  CGC  TTC  CTG  AAG  GAC  AGT  TTG  TAC  ACC  GAA  GGA  ATC  CTG  ATT         675
Lys  Arg  Phe  Leu  Lys  Asp  Ser  Leu  Tyr  Thr  Glu  Gly  Ile  Leu  Ile
          215                      220                      225

CTG  TGG  GAC  CCA  TCT  GTG  TAT  CAT  GCA  GAC  ATT  CCG  CAG  TGG  TAT         720
Leu  Trp  Asp  Pro  Ser  Val  Tyr  His  Ala  Asp  Ile  Pro  Gln  Trp  Tyr
          230                      235                      240

CAG  AAG  CCA  GAC  TAC  AAC  TTC  TTC  GAA  ACC  TAT  AAG  AGT  TAC  CGA         765
Gln  Lys  Pro  Asp  Tyr  Asn  Phe  Phe  Glu  Thr  Tyr  Lys  Ser  Tyr  Arg
          245                      250                      255

AGG  CTT  CAC  CCC  AGC  CAG  CCT  TTT  TAC  ATC  CTC  AAG  CCC  CAG  ATG         810
Arg  Leu  His  Pro  Ser  Gln  Pro  Phe  Tyr  Ile  Leu  Lys  Pro  Gln  MET
          260                      265                      270

CCA  TGG  GAA  CTA  TGG  GAC  ATC  ATT  CAG  GAA  ATC  TCT  CCA  GAT  CTG         855
Pro  Trp  Glu  Leu  Trp  Asp  Ile  Ile  Gln  Glu  Ile  Ser  Pro  Asp  Leu
          275                      280                      285

ATT  CAG  CCG  AAT  CCC  CCA  TCC  TCC  GGC  ATG  CTG  GGT  ATC  ATC  ATT         900
Ile  Gln  Pro  Asn  Pro  Pro  Ser  Ser  Gly  MET  Leu  Gly  Ile  Ile  Ile
          290                      295                      300

ATG  ATG  ACG  CTG  TGT  GAC  CAA  GTT  GAT  ATT  TAC  GAG  TTC  CTC  CCA         945
MET  MET  Thr  Leu  Cys  Asp  Gln  Val  Asp  Ile  Tyr  Glu  Phe  Leu  Pro
          305                      310                      315

TCC  AAG  CGC  AAG  ACA  GAT  GTG  TGC  TAC  TAT  CAC  CAG  AAG  TTC  TTT         990
Ser  Lys  Arg  Lys  Thr  Asp  Val  Cys  Tyr  Tyr  His  Gln  Lys  Phe  Phe
          320                      325                      330

GAC  AGC  GCC  TGC  ACG  ATG  GGT  GCC  TAC  CAT  CCG  CTC  CTC  TTC  GAG        1035
Asp  Ser  Ala  Cys  Thr  MET  Gly  Ala  Tyr  His  Pro  Leu  Leu  Phe  Glu
          335                      340                      345

AAG  AAT  ATG  GTG  AAG  CAT  CTC  AAT  GAG  GGA  ACA  GAT  GAA  GAC  ATT        1080
Lys  Asn  MET  Val  Lys  His  Leu  Asn  Glu  Gly  Thr  Asp  Glu  Asp  Ile
          350                      355                      360

TAT  TTG  TTT  GGG  AAA  GCT  ACC  CTG  TCT  GGC  TTC  CGG  AAC  AAT  CGC        1125
Tyr  Leu  Phe  Gly  Lys  Ala  Thr  Leu  Ser  Gly  Phe  Arg  Asn  Asn  Arg
          365                      370                      375

TGT  TGA  GCCAGGGATC  CTCAT                                                      1146
Cys
```

( 2 ) INFORMATION FOR SEQ ID NO:5:

( i ) SEQUENCE CHARACTERISTICS:
        ( A ) LENGTH: 566 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

```
MET  Gly  Phe  Leu  Ile  Arg  Arg  Leu  Pro  Lys  Asp  Ser  Arg  Ile  Phe
 1              5                        10                       15
```

| | | | | | | | | | | | | | | |
|---|---|---|---|---|---|---|---|---|---|---|---|---|---|---|
| Arg | Trp | Leu | Leu | Ile<br>20 | Leu | Thr | Val | Phe | Ser<br>25 | Phe | Ile | Ile | Thr | Ser<br>30 |
| Phe | Ser | Ala | Leu | Phe<br>35 | Gly | MET | Glu | Lys | Ser<br>40 | Ile | Phe | Arg | Gln | Leu<br>45 |
| Lys | Ile | Tyr | Gln | Ser<br>50 | Ile | Ala | His | MET | Leu<br>55 | Gln | Val | Asp | Thr | Gln<br>60 |
| Asp | Gln | Gln | Gly | Ser<br>65 | Asn | Tyr | Ser | Ala | Asn<br>70 | Gly | Arg | Ile | Ser | Lys<br>75 |
| Val | Gly | Leu | Glu | Arg<br>80 | Asp | Ile | Ala | Trp | Leu<br>85 | Glu | Leu | Asn | Thr | Ala<br>90 |
| Val | Ser | Thr | Pro | Ser<br>95 | Gly | Glu | Gly | Lys | Glu<br>100 | Glu | Gln | Lys | Lys | Thr<br>105 |
| Val | Lys | Pro | Val | Ala<br>110 | Lys | Val | Glu | Glu | Ala<br>115 | Lys | Glu | Lys | Val | Thr<br>120 |
| Val | Lys | Pro | Phe | Pro<br>125 | Glu | Val | MET | Gly | Ile<br>130 | Thr | Asn | Thr | Thr | Ala<br>135 |
| Ser | Thr | Ala | Ser | Val<br>140 | Val | Glu | Arg | Thr | Lys<br>145 | Glu | Lys | Thr | Thr | Ala<br>150 |
| Arg | Pro | Val | Pro | Gly<br>155 | Val | Gly | Glu | Ala | Asp<br>160 | Gly | Lys | Arg | Thr | Thr<br>165 |
| Ile | Ala | Leu | Pro | Ser<br>170 | MET | Lys | Glu | Asp | Lys<br>175 | Glu | Lys | Ala | Thr | Val<br>180 |
| Lys | Pro | Ser | Phe | Gly<br>185 | MET | Lys | Val | Ala | His<br>190 | Ala | Asn | Ser | Thr | Ser<br>195 |
| Lys | Asp | Lys | Pro | Lys<br>200 | Ala | Glu | Glu | Pro | Pro<br>205 | Ala | Ser | Val | Lys | Ala<br>210 |
| Ile | Arg | Pro | Val | Thr<br>215 | Gln | Ala | Ala | Thr | Val<br>220 | Thr | Glu | Lys | Lys | Lys<br>225 |
| Leu | Arg | Ala | Ala | Asp<br>230 | Phe | Lys | Thr | Glu | Pro<br>235 | Gln | Trp | Asp | Phe | Asp<br>240 |
| Asp | Glu | Tyr | Ile | Leu<br>245 | Asp | Ser | Ser | Ser | Pro<br>250 | Val | Ser | Thr | Cys | Ser<br>255 |
| Glu | Ser | Val | Arg | Ala<br>260 | Lys | Ala | Ala | Lys | Ser<br>265 | Asp | Trp | Leu | Arg | Asp<br>270 |
| Leu | Phe | Leu | Pro | Asn<br>275 | Ile | Thr | Leu | Phe | Ile<br>280 | Asp | Lys | Ser | Tyr | Phe<br>285 |
| Asn | Val | Ser | Glu | Trp<br>290 | Asp | Arg | Leu | Glu | His<br>295 | Phe | Ala | Pro | Pro | Tyr<br>300 |
| Gly | Phe | MET | Glu | Leu<br>305 | Asn | Tyr | Ser | Leu | Val<br>310 | Glu | Glu | Val | MET | Ser<br>315 |
| Arg | Leu | Pro | Pro | Asn<br>320 | Pro | His | Gln | Gln | Leu<br>325 | Leu | Leu | Ala | Asn | Ser<br>330 |
| Ser | Ser | Asn | Val | Ser<br>335 | Thr | Cys | Ile | Ser | Cys<br>340 | Ala | Val | Val | Gly | Asn<br>345 |
| Gly | Gly | Ile | Leu | Asn<br>350 | Asn | Ser | Gly | MET | Gly<br>355 | Gln | Glu | Ile | Asp | Ser<br>360 |
| His | Asp | Tyr | Val | Phe<br>365 | Arg | Val | Ser | Gly | Ala<br>370 | Val | Ile | Lys | Gly | Tyr<br>375 |
| Glu | Lys | Asp | Val | Gly<br>380 | Thr | Lys | Thr | Ser | Phe<br>385 | Tyr | Gly | Phe | Thr | Ala<br>390 |
| Tyr | Ser | Leu | Val | Ser<br>395 | Ser | Leu | Gln | Asn | Leu<br>400 | Gly | His | Lys | Gly | Phe<br>405 |
| Lys | Lys | Ile | Pro | Gln<br>410 | Gly | Lys | His | Ile | Arg<br>415 | Tyr | Ile | His | Phe | Leu<br>420 |

| | | | | | | | | | | | | | | |
|---|---|---|---|---|---|---|---|---|---|---|---|---|---|---|
|Glu|Ala|Val|Arg|Asp 425|Tyr|Glu|Trp|Leu|Lys 430|Ala|Leu|Leu|Leu|Asp 435|
|Lys|Asp|Ile|Arg|Lys 440|Gly|Phe|Leu|Asn|Tyr 445|Tyr|Gly|Arg|Arg|Pro 450|
|Arg|Glu|Arg|Phe|Asp 455|Glu|Asp|Phe|Thr|MET 460|Asn|Lys|Tyr|Leu|Val 465|
|Ala|His|Pro|Asp|Phe 470|Leu|Arg|Tyr|Leu|Lys 475|Asn|Arg|Phe|Leu|Lys 480|
|Ser|Lys|Asn|Leu|Gln 485|Lys|Pro|Tyr|Trp|Arg 490|Leu|Tyr|Arg|Pro|Thr 495|
|Thr|Gly|Ala|Leu|Leu 500|Leu|Leu|Thr|Ala|Leu 505|His|Leu|Cys|Asp|Arg 510|
|Val|Ser|Ala|Tyr|Gly 515|Tyr|Ile|Thr|Glu|Gly 520|His|Gln|Lys|Tyr|Ser 525|
|Asp|His|Tyr|Tyr|Asp 530|Lys|Glu|Trp|Lys|Arg 535|Leu|Val|Phe|Tyr|Val 540|
|Asn|His|Asp|Phe|Asn 545|Leu|Glu|Lys|Gln|Val 550|Trp|Lys|Arg|Leu|His 555|
|Asp|Glu|Asn|Ile|MET 560|Lys|Leu|Tyr|Gln|Arg 565|Ser| | | | |

(2) INFORMATION FOR SEQ ID NO:6:

(i) SEQUENCE CHARACTERISTICS:
        (A) LENGTH: 355 amino acids
        (B) TYPE: amino acid
        (C) STRANDEDNESS: single
        (D) TOPOLOGY: linear (xi) SEQUENCE DESCRIPTION: SEQ ID NO:6:

| | | | | | | | | | | | | | | |
|---|---|---|---|---|---|---|---|---|---|---|---|---|---|---|
|MET 1|Lys|Phe|Ser|Trp 5|Val|MET|Phe|Phe|Leu 10|MET|Ala|Val|Val|Thr 15|
|Gly|Val|Asn|Ser|Glu 20|Phe|Thr|Glu|Pro|Gln 25|Trp|Asp|Phe|Asp|Asp 30|
|Glu|Tyr|Ile|Leu|Asp 35|Ser|Ser|Ser|Pro|Val 40|Ser|Thr|Cys|Ser|Glu 45|
|Ser|Val|Arg|Ala|Lys 50|Ala|Ala|Lys|Ser|Asp 55|Trp|Leu|Arg|Asp|Leu 60|
|Phe|Leu|Pro|Asn|Ile 65|Thr|Leu|Phe|Ile|Asp 70|Lys|Ser|Tyr|Phe|Asn 75|
|Val|Ser|Glu|Trp|Asp 80|Arg|Leu|Glu|His|Phe 85|Ala|Pro|Pro|Tyr|Gly 90|
|Phe|MET|Glu|Leu|Asn 95|Tyr|Ser|Leu|Val|Glu 100|Glu|Val|MET|Ser|Arg 105|
|Leu|Pro|Pro|Asn|Pro 110|His|Gln|Gln|Leu|Leu 115|Leu|Ala|Asn|Ser|Ser 120|
|Ser|Asn|Val|Ser|Thr 125|Cys|Ile|Ser|Cys|Ala 130|Val|Val|Gly|Asn|Gly 135|
|Gly|Ile|Leu|Asn|Asn 140|Ser|Gly|MET|Gly|Gln 145|Glu|Ile|Asp|Ser|His 150|
|Asp|Tyr|Val|Phe|Arg 155|Val|Ser|Gly|Ala|Val 160|Ile|Lys|Gly|Tyr|Glu 165|
|Lys|Asp|Val|Gly|Thr 170|Lys|Thr|Ser|Phe|Tyr 175|Gly|Phe|Thr|Ala|Tyr 180|
|Ser|Leu|Val|Ser|Ser 185|Leu|Gln|Asn|Leu|Gly 190|His|Lys|Gly|Phe|Lys 195|

| Lys | Ile | Pro | Gln | Gly<br>200 | Lys | His | Ile | Arg<br>205 | Tyr | Ile | His | Phe | Leu | Glu<br>210 |
|---|---|---|---|---|---|---|---|---|---|---|---|---|---|---|
| Ala | Val | Arg | Asp | Tyr<br>215 | Glu | Trp | Leu | Lys<br>220 | Ala | Leu | Leu | Leu | Asp | Lys<br>225 |
| Asp | Ile | Arg | Lys | Gly<br>230 | Phe | Leu | Asn | Tyr<br>235 | Tyr | Gly | Arg | Arg | Pro | Arg<br>240 |
| Glu | Arg | Phe | Asp | Glu<br>245 | Asp | Phe | Thr | MET<br>250 | Asn | Lys | Tyr | Leu | Val | Ala<br>255 |
| His | Pro | Asp | Phe | Leu<br>260 | Arg | Tyr | Leu | Lys<br>265 | Asn | Arg | Phe | Leu | Lys | Ser<br>270 |
| Lys | Asn | Leu | Gln | Lys<br>275 | Pro | Tyr | Trp | Arg<br>280 | Leu | Tyr | Arg | Pro | Thr | Thr<br>285 |
| Gly | Ala | Leu | Leu | Leu<br>290 | Leu | Thr | Ala | Leu<br>295 | His | Leu | Cys | Asp | Arg | Val<br>300 |
| Ser | Ala | Tyr | Gly | Tyr<br>305 | Ile | Thr | Glu | Gly<br>310 | His | Gln | Lys | Tyr | Ser | Asp<br>315 |
| His | Tyr | Tyr | Asp | Lys<br>320 | Glu | Trp | Lys | Arg<br>325 | Leu | Val | Phe | Tyr | Val | Asn<br>330 |
| His | Asp | Phe | Asn | Leu<br>335 | Glu | Lys | Gln | Val<br>340 | Trp | Lys | Arg | Leu | His | Asp<br>345 |
| Glu | Asn | Ile | MET | Lys<br>350 | Leu | Tyr | Gln | Arg<br>355 | Ser | | | | | |

( 2 ) INFORMATION FOR SEQ ID NO:7:

( i ) SEQUENCE CHARACTERISTICS:
        ( A ) LENGTH: 404 amino acids
        ( B ) TYPE: amino acid
        ( C ) STRANDEDNESS: single
        ( D ) TOPOLOGY: linear ( v i ) ORIGINAL SOURCE:
        ( A ) ORGANISM: G. gallus (chicken)

( x i ) SEQUENCE DESCRIPTION: SEQ ID NO:7:

| MET<br>1 | Gly | Ser | Pro | Arg<br>5 | Trp | Lys | Arg | Phe | Cys<br>10 | Phe | Leu | Leu | Leu | Ala<br>15 |
|---|---|---|---|---|---|---|---|---|---|---|---|---|---|---|
| Ala | Phe | Thr | Ser | Ser<br>20 | Leu | Leu | Leu | Tyr | Gly<br>25 | His | Tyr | Tyr | Ala | Thr<br>30 |
| Val | Asp | Val | Arg | Ser<br>35 | Gly | Pro | Arg | Val | Val<br>40 | Thr | Ser | Leu | Leu | Gln<br>45 |
| Pro | Glu | Leu | Leu | Phe<br>50 | Leu | Val | Arg | Pro | Asp<br>55 | Thr | Pro | His | Pro | Asp<br>60 |
| Asn | Ser | His | His | Lys<br>65 | Glu | Leu | Arg | Gly | Thr<br>70 | Val | Lys | Ser | Arg | Glu<br>75 |
| Phe | Phe | Ser | Gln | Pro<br>80 | Ser | Ser | Glu | Leu | Glu<br>85 | Lys | Pro | Lys | Pro | Ser<br>90 |
| Gly | Lys | Gln | Pro | Thr<br>95 | Pro | Cys | Pro | Arg | Ser<br>100 | Val | Ala | Ala | Thr | Ala<br>105 |
| Lys | Ala | Asp | Pro | Thr<br>110 | Phe | Gly | Glu | Leu | Phe<br>115 | Gln | Phe | Asp | Ile | Pro<br>120 |
| Val | Leu | Met | Trp | Asp<br>125 | Gln | His | Phe | Asn | Pro<br>130 | Glu | Thr | Trp | Asp | Arg<br>135 |
| Leu | Lys | Ala | Arg | Arg<br>140 | Val | Pro | Tyr | Gly | Trp<br>145 | Gln | Gly | Leu | Ser | Gln<br>150 |
| Ala | Ala | Val | Gly | Ser<br>155 | Thr | Leu | Arg | Leu | Leu<br>160 | Asn | Thr | Ser | Ser | Asn<br>165 |

| | | | | | | | | | | | | | | |
|---|---|---|---|---|---|---|---|---|---|---|---|---|---|---|
|Thr|Arg|Leu|Phe|Asp|Arg|His|Leu|Phe|Pro|Gly|Gly|Cys|Ile|Arg|
| | | |   |170|   |   |   |   |175|   |   |   |   |180|
|Cys|Ala|Val|Val|Gly|Asn|Gly|Gly|Ile|Leu|Asn|Gly|Ser|Arg|Gln|
| | | |   |185|   |   |   |   |190|   |   |   |   |195|
|Gly|Arg|Ala|Ile|Asp|Ala|His|Asp|Leu|Val|Phe|Arg|Leu|Asn|Gly|
| | | |   |200|   |   |   |   |205|   |   |   |   |210|
|Ala|Ile|Thr|Lys|Gly|Phe|Glu|Glu|Asp|Val|Gly|Ser|Lys|Val|Ser|
| | | |   |215|   |   |   |   |220|   |   |   |   |225|
|Phe|Tyr|Gly|Phe|Thr|Val|Asn|Thr|Met|Lys|Asn|Ser|Leu|Ile|Ala|
| | | |   |230|   |   |   |   |235|   |   |   |   |240|
|Tyr|Glu|Ala|Tyr|Gly|Phe|Thr|Arg|Thr|Pro|Gln|Gly|Lys|Asp|Leu|
| | | |   |245|   |   |   |   |250|   |   |   |   |255|
|Lys|Tyr|Ile|Phe|Ile|Pro|Ser|Asp|Ala|Arg|Asp|Tyr|Ile|Met|Leu|
| | | |   |260|   |   |   |   |265|   |   |   |   |270|
|Arg|Ser|Ala|Ile|Gln|Gly|Ser|Pro|Val|Pro|Glu|Gly|Leu|Asp|Lys|
| | | |   |275|   |   |   |   |280|   |   |   |   |285|
|Gly|Asp|Glu|Pro|Gln|Lys|Tyr|Phe|Gly|Leu|Glu|Ala|Ser|Ala|Glu|
| | | |   |290|   |   |   |   |295|   |   |   |   |300|
|Lys|Phe|Lys|Leu|Leu|His|Pro|Asp|Phe|Leu|His|Tyr|Leu|Thr|Thr|
| | | |   |305|   |   |   |   |310|   |   |   |   |315|
|Arg|Phe|Leu|Arg|Ser|Glu|Leu|Leu|Asp|Met|Gln|Tyr|Gly|His|Leu|
| | | |   |320|   |   |   |   |325|   |   |   |   |330|
|Tyr|Met|Pro|Ser|Thr|Gly|Ala|Leu|Met|Leu|Leu|Thr|Ala|Leu|His|
| | | |   |335|   |   |   |   |340|   |   |   |   |345|
|Thr|Cys|Asp|Gln|Val|Ser|Ala|Tyr|Gly|Phe|Ile|Thr|Ala|Asn|Tyr|
| | | |   |350|   |   |   |   |355|   |   |   |   |360|
|Glu|Gln|Phe|Ser|Asp|His|Tyr|Tyr|Glu|Pro|Glu|Lys|Lys|Pro|Leu|
| | | |   |365|   |   |   |   |370|   |   |   |   |375|
|Val|Phe|Tyr|Ala|Asn|His|Asp|Met|Leu|Leu|Glu|Ala|Glu|Leu|Trp|
| | | |   |380|   |   |   |   |385|   |   |   |   |390|
|Arg|Ser|Leu|His|Arg|Ala|Gly|Ile|Met|Glu|Leu|Tyr|Gln|Arg| |
| | | |   |395|   |   |   |   |400|   |   |   |   | |

( 2 ) INFORMATION FOR SEQ ID NO:8:

( i ) SEQUENCE CHARACTERISTICS:
        ( A ) LENGTH: 376 amino acids
        ( B ) TYPE: amino acid
        ( C ) STRANDEDNESS: single
        ( D ) TOPOLOGY: linear ( v i ) ORIGINAL SOURCE:
        ( A ) ORGANISM: mouse ( x i ) SEQUENCE DESCRIPTION: SEQ ID NO:8:

| | | | | | | | | | | | | | | |
|---|---|---|---|---|---|---|---|---|---|---|---|---|---|---|
|MET|Gly|Ser|Asp|Tyr|Glu|Ala|Leu|Thr|Leu|Gln|Ala|Lys|Val|Phe|
|1| | |   |5|   |   |   |   |10|   |   |   |   |15|
|Gln|MET|Pro|Lys|Ser|Gln|Glu|Lys|Val|Ala|Val|Gly|Pro|Ala|Pro|
| | | |   |20|   |   |   |   |25|   |   |   |   |30|
|Gln|Ala|Val|Phe|Ser|Asn|Ser|Lys|Gln|Asp|Pro|Lys|Glu|Gly|Val|
| | | |   |35|   |   |   |   |40|   |   |   |   |45|
|Gln|Ile|Leu|Ser|Tyr|Pro|Arg|Val|Thr|Ala|Lys|Val|Lys|Pro|Gln|
| | | |   |50|   |   |   |   |55|   |   |   |   |60|
|Pro|Ser|Leu|Gln|Val|Trp|Asp|Lys|Asp|Ser|Thr|Tyr|Ser|Lys|Leu|
| | | |   |65|   |   |   |   |70|   |   |   |   |75|
|Asn|Pro|Arg|Leu|Leu|Lys|Ile|Trp|Arg|Asn|Tyr|Leu|Asn|MET|Asn|
| | | |   |80|   |   |   |   |85|   |   |   |   |90|

| | | | | | | | | | | | | | | |
|---|---|---|---|---|---|---|---|---|---|---|---|---|---|---|
| Lys | Tyr | Lys | Val | Ser 95 | Tyr | Lys | Gly | Pro | Gly 100 | Pro | Gly | Val | Arg | Phe 105 |
| Ser | Val | Glu | Gly | Leu 110 | Arg | Cys | His | Leu | Arg 115 | Asp | His | Val | Asn | Val 120 |
| Ser | MET | Ile | Glu | Ala 125 | Thr | Asp | Ser | Pro | Phe 130 | Asn | Thr | Thr | Glu | Trp 135 |
| Glu | Gly | Tyr | Leu | Pro 140 | Lys | Glu | Thr | Phe | Arg 145 | Thr | Lys | Ala | Gly | Pro 150 |
| Cys | Thr | Lys | Cys | Ala 155 | Val | Val | Ser | Ser | Ala 160 | Gly | Ser | Leu | Lys | Asn 165 |
| Ser | Gln | Leu | Gly | Arg 170 | Glu | Ile | Asp | Asn | His 175 | Asp | Ala | Val | Leu | Arg 180 |
| Phe | Asn | Gly | Ala | Pro 185 | Thr | Asp | Asn | Phe | Gln 190 | Gln | Asp | Val | Gly | Thr 195 |
| Lys | Thr | Thr | Ile | Arg 200 | Leu | Val | Asn | Ser | Gln 205 | Leu | Val | Thr | Thr | Glu 210 |
| Lys | Arg | Phe | Leu | Lys 215 | Asp | Ser | Leu | Tyr | Thr 220 | Glu | Gly | Ile | Leu | Ile 225 |
| Leu | Trp | Asp | Pro | Ser 230 | Val | Tyr | His | Ala | Asp 235 | Ile | Pro | Gln | Trp | Tyr 240 |
| Gln | Lys | Pro | Asp | Tyr 245 | Asn | Phe | Phe | Glu | Thr 250 | Tyr | Lys | Ser | Tyr | Arg 255 |
| Arg | Leu | His | Pro | Ser 260 | Gln | Pro | Phe | Tyr | Ile 265 | Leu | Lys | Pro | Gln | MET 270 |
| Pro | Trp | Glu | Leu | Trp 275 | Asp | Ile | Ile | Gln | Glu 280 | Ile | Ser | Pro | Asp | Leu 285 |
| Ile | Gln | Pro | Asn | Pro 290 | Pro | Ser | Ser | Gly | MET 295 | Leu | Gly | Ile | Ile | Ile 300 |
| MET | MET | Thr | Leu | Cys 305 | Asp | Gln | Val | Asp | Ile 310 | Tyr | Glu | Phe | Leu | Pro 315 |
| Ser | Lys | Arg | Lys | Thr 320 | Asp | Val | Cys | Tyr | Tyr 325 | His | Gln | Lys | Phe | Phe 330 |
| Asp | Ser | Ala | Cys | Thr 335 | MET | Gly | Ala | Tyr | His 340 | Pro | Leu | Leu | Phe | Glu 345 |
| Lys | Asn | MET | Val | Lys 350 | His | Leu | Asn | Glu | Gly 355 | Thr | Asp | Glu | Asp | Ile 360 |
| Tyr | Leu | Phe | Gly | Lys 365 | Ala | Thr | Leu | Ser | Gly 370 | Phe | Arg | Asn | Asn | Arg 375 |
| Cys | | | | | | | | | | | | | | |